US009909168B2

(12) United States Patent
Notomi et al.

(10) Patent No.: US 9,909,168 B2
(45) Date of Patent: Mar. 6, 2018

(54) METHOD OF SYNTHESIZING NUCLEIC ACID

(75) Inventors: Tsugunori Notomi, Tochigi (JP); Tetsu Hase, Otawara (JP)

(73) Assignee: EIKEN KAGAKU KABUSHIKI KAISHA, Tokyo (JP)

( * ) Notice: Subject to any disclaimer, the term of this patent is extended or adjusted under 35 U.S.C. 154(b) by 732 days.

(21) Appl. No.: 12/331,196

(22) Filed: Dec. 9, 2008

(65) Prior Publication Data

US 2009/0098566 A1 Apr. 16, 2009

Related U.S. Application Data

(60) Division of application No. 10/782,040, filed on Feb. 19, 2004, now Pat. No. 7,494,790, which is a division of application No. 10/132,561, filed on Apr. 24, 2002, now Pat. No. 6,974,670, which is a continuation of application No. 09/530,061, filed as application No. PCT/JP99/06213 on Nov. 8, 1999, now Pat. No. 6,410,278.

(30) Foreign Application Priority Data

Nov. 9, 1998 (JP) ..................................... 10317476

(51) Int. Cl.
*C12Q 1/68* (2006.01)
*C12N 15/10* (2006.01)

(52) U.S. Cl.
CPC ........... *C12Q 1/6844* (2013.01); *C12N 15/10* (2013.01); *C12Q 1/6853* (2013.01); *C12Q 2525/161* (2013.01); *C12Q 2527/101* (2013.01); *C12Q 2527/125* (2013.01); *C12Q 2531/119* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,104,791 A | 4/1992 | Abbott et al. | |
| 5,270,184 A * | 12/1993 | Walker et al. | 435/91.2 |
| 5,474,796 A * | 12/1995 | Brennan | 427/2.13 |
| 5,525,462 A | 6/1996 | Takareda et al. | |
| 5,595,891 A | 1/1997 | Rose et al. | |
| 5,612,199 A | 3/1997 | Western et al. | |
| 5,648,211 A | 7/1997 | Fraiser et al. | |
| 5,674,683 A | 10/1997 | Kool | |
| 5,712,124 A | 1/1998 | Walker | |
| 5,714,323 A | 2/1998 | Ohshima et al. | |
| 5,728,522 A | 3/1998 | Del Vecchio et al. | |
| 5,744,311 A | 4/1998 | Fraiser et al. | |
| 5,786,183 A | 7/1998 | Ryder | |
| 5,849,547 A | 12/1998 | Cleuziat et al. | |
| 5,866,331 A | 2/1999 | Singer et al. | |
| 5,874,260 A | 2/1999 | Cleuziat et al. | |
| 5,972,618 A | 10/1999 | Bloch | |
| 6,025,139 A | 2/2000 | Yager et al. | |
| 6,033,881 A | 3/2000 | Himmler et al. | |
| 6,063,603 A | 5/2000 | Davey et al. | |
| 6,197,563 B1 | 3/2001 | Erlich et al. | |
| 6,270,962 B1 | 8/2001 | Chamberlin et al. | |
| 6,410,278 B1 | 6/2002 | Notomi et al. | |
| 6,743,605 B1 | 6/2004 | Rabbani et al. | |
| 6,794,133 B1 | 9/2004 | Ausubel et al. | |
| 6,974,670 B2 | 12/2005 | Notomi et al. | |
| 7,067,117 B1 | 6/2006 | Grainger et al. | |
| 2003/0104460 A1 | 6/2003 | Rabbani et al. | |
| 2003/0165936 A1 | 9/2003 | Rabbani et al. | |
| 2003/0165938 A1 | 9/2003 | Rabbani et al. | |
| 2003/0165939 A1 | 9/2003 | Rabbani et al. | |
| 2003/0170681 A1 | 9/2003 | Rabbani et al. | |
| 2003/0170682 A1 | 9/2003 | Rabbani et al. | |
| 2003/0207292 A1 | 11/2003 | Notomi et al. | |
| 2006/0160084 A1 | 7/2006 | Mitani et al. | |

FOREIGN PATENT DOCUMENTS

| | | |
|---|---|---|
| EP | 0549107 A1 | 10/1992 |
| EP | 0678582 A | 10/1995 |
| EP | 0 713 922 | 5/1996 |
| EP | 0971039 A2 | 1/2000 |
| JP | 5-211873 | 8/1993 |
| JP | 9-168400 | 6/1997 |
| JP | 10-510161 | 10/1998 |
| WO | 9503426 A2 | 2/1995 |
| WO | WO-95/05391 | 2/1995 |
| WO | WO 9503426 A2 * | 2/1995 |
| WO | 9601327 | 1/1996 |
| WO | WO-96/17079 | 6/1996 |
| WO | WO-96/17959 | 6/1996 |
| WO | WO-96/31622 | 10/1996 |
| WO | 9704131 | 2/1997 |
| WO | 9966071 | 12/1999 |

OTHER PUBLICATIONS

Stratagene ("Gene Characterization Kits" 1988).*
Wei et al. (Cancer Res. Nov. 1, 1995;55(21):5025-9).*
Merriam-Webster, definition of region, attached, available at https://www.merriam-webster.com/dictionary/region?utm_campaign=sd&utm_medium=serp&utm_source=jsonld.*
NCBI Accession No. AH008265 (Oct. 6, 1999).*

(Continued)

*Primary Examiner* — Aaron Priest
(74) *Attorney, Agent, or Firm* — Baker & Hostetler LLP

(57) ABSTRACT

The present invention relates to an oligonucleotide having a novel structure and a method of synthesizing nucleic acid by using the same as a primer. This oligonucleotide is provided at the 5'-side of the primer with a nucleotide sequence substantially the same as a region synthesized with this primer as the origin of synthesis. The present invention realizes synthesis of nucleic acid based on an isothermal reaction with a simple constitution of reagents. Further, the present invention provides a method of synthesizing highly specific nucleic acid on the basis of this method of synthesizing nucleic acid.

8 Claims, 18 Drawing Sheets

(56) References Cited

OTHER PUBLICATIONS

Weiner et al. (Kits and their unique role in molecular biology: a brief retrospective, BioTechniques 44:701-704 (25th Anniversary Issue, Apr. 2008)).*
Notomi et al., "Loop-Mediated Isothermal Amplification of DNA," Nucleic Acids Res. 28(12):e63 (2000).
Whitcombe et al., "Detection of PCT Products Using Self-Probing Amplicons and Fluorescence," Nature Biotechnology 17:804-807 (1999).
Lizardi et al., "Mutation Detection and Single-Molecule Counting Using Isothermal Rolling-Circle Amplification," Nature Genetics 19:225-232 (1998).
Stratagene Catalog, "Gene Characterization Kits," p. 39 (1988).
Walker et al., "Strand Displacement Amplification—An Isothermal, in vitro DNA Amplification Technique," Nucleic Acids Res. 20(7):1691-1696 (1992).
Tattersall et al., "Rolling Hairpin Model for Replication of Parvovirus and Linear Chromosomal DNA," Nature 263:106-109 (1976).
Request for Inter Partes Reexamination of U.S. Pat. No. 6,974,670 (assigned Control No. 95/001146).
Declaration of Dr. Keith C. Beckman (with Exhibit A), as submitted in Reexamination Control No. 95/001146.
Decision on Petition, as entered in Reexamination Control No. 95/001146.
Office Action in Reexamination Control No. 95/001146 (dated Sep. 24, 2009).
Borghesi-Nicoletti, Chiara et al. (1992). "Oligonucleotide Hybridization Used to Detect Short Non-Contiguous Sequences." *BioFeedback: Bio Techniques*. 12(4):, 474-477.
US Office Action issued in U.S. Appl. No. 15/392,758 dated Feb. 2, 2017.
Merriam-Webster, definition of region, attached, available at https://www.merriamwebster.com/dictionary/region?utm_campaign=sd&utm_medium=serp&utm_source=jsonid.
NCBI Accession No. AH008265, attached (Oct. 6, 1999).
Compton, J. (Mar. 7, 1991). "Nucleic Acid Sequence-Based Amplification." *Nature*. 350:91-92.
Kornerg, A. et al.. (1991). *DNA Replication*. 2nd Ed., W.H. Freeman and Company. New York. 700-716 and cover page.
Laffler Tg et al. (1993). "The Ligase Chain Reaction in DNA-based diagnosis." *Ann Biol. Clin.* 50:821-826.
Morrical, S., et al. (Jul. 25, 1991). "Amplification of Snap-back DNA Synthesis Reactions by the uvsX Recombinase of Bacteriophage T4*." *The Journal of Biological Chemistry*. 14031-14038.
Nakayama, H. (1998). "The PCR Which Really Increases." Bioexperiment Illustrated 3+. 2nd Ed. 25-26, 163-165, 169 (English translation of portions of pp. 163 and 164).
Raney, K. D. (1994). "A Flourescence-based Assay for Monitoring Helicase Activity," *Proc. Nat'l. Acad. Sci. USA*. 91:6644-6648.
Ricca, G. et al. (Feb. 1982). "Simple Rapid Method for the Synthesis of Radioactively Labeled cDNA Hybridization Probes Utilizing Bacteriophage M13mp7." *Proc. Natl. Acad. Sci.* USA. 79:724-728.
Saiki, R. et al. (Dec. 20, 1985)."Enzymatic Amplification of β-Globin Genomic Sequences and Restriction Site Analysis for Diagnosis of Sickle Cell Anemia." *Science*. 230:1350-1354.
Uhlmann, E. (1988). "An Alternative Approach in Gene Synthesis: Use of Long Selfpriming Oligodeoxynucleotides for the Construction of Double-Standed DNA." *Gene*. 71:29-40.
Walker, G. T. (1992). "Isothermal in vitro amplification of DNA by a restriction enzyme/DNA polymerase system," *Proc. Natl. Acad. Sci.* USA. 89:392-396.
Webster's II New Riverside University Dictionary, 1984. P. 388 (meaning of the word "Displace").
Notomi, U.S. Office Action dated Feb. 15, 2001, directed to U.S. Appl. No. 09/530,061; 16 pages.
Notomi, U.S. Office Action dated Sep. 7, 2001, directed to U.S. Appl. No. 09/530,061; 11 pages.
Request for Ex Parte Reexamination of U.S. Pat. No. 6,410,278 to Notomi et al. (Control No. 90/010,702); 597 pages.
Order Granting Request for Ex Parte Reexamination of U.S. Pat. No. 6,410,278 to Notomi et al. (Control No. 90/010,702); 9 pages.
Notomi, U.S. Office Action dated Sep. 2, 2003, directed to U.S. Appl. No. 10/132,561; 8 pages.
Notomi, U.S. Office Action dated Feb. 25, 2005, directed to U.S. Appl. No. 10/132,561; 10 pages.
Notomi, U.S. Office Action dated Jan. 30, 2007, directed to U.S. Appl. No. 10/782,040; 13 pages.
Notomi, U.S. Office Action dated Sep. 19, 2007, directed to U.S. Appl. No. 10/782,040; 11 pages.
Notomi, U.S. Office Action dated Jun. 25, 2008, directed to U.S. Appl. No. 10/782,040; 9 pages.

* cited by examiner

Fig. 7

```
6001 GCGCCCAATA CGCAAACCGC CTCTCCCCGC GCGTTGGCCG ATTCATTAAT GCAGCTGGCA

6061 CGACAGGTTT CCCGACTGGA AAGCGGGCAG TGAGCGCAAC GCAATTAATG TGAGTTAGCT
                                                    M13F3              M13F2
6121 CACTCATTAG GCACCCCAGG CTTTACACTT TATGCTTCCG GCTCGTATGT TGTGTGGAAT

6181 TGTGAGCGGA TAACAATTTC ACACAGGAAA CAGCTATGAC CATGATTACG AATTCGAGCT
                       M13F1c
6241 CGGTACCCGG GGATCCTCTA GAGTCGACCT GCAGGCATGC AAGCTTGGCA CTGGCCGTCG
               M13R1c
6301 TTTTACAACG TCGTGACTGG GAAAACCCTG GCGTTACCCA ACTTAATCGC CTTGCAGCAC
                                        M13R2              M13R3
6361 ATCCCCCTTT CGCCAGCTGG CGTAATAGCG AAGAGGCCCG CACCGATCGC CCTTCCCAAC

6421 AGTTGCGCAG CCTGAATGGC GAATGGCGCT TTGCCTGGTT TCCGCACCA GAAGCGGTGC

6481 CGGAAAGCTG GCTGGAGTGC GATCTTCCTG AGGCCGATAC GGTCGTCGTC CCCTCAAACT

6541 GGCAGATGCA CGGTTACGAT GCGCCCATCT ACACCAACGT AACCTATCCC ATTACGGTCA
```

Fig. 11

```
  1 CTCCTTGACA CCGCCTCTGC TCTGTATCGG GAGGCCTTAG AGTCTCCGGA ACATTGTTCA

61 CCTCACCATA CAGCACTCAG GCAAGCTATT CTGTGTTGGG GTGAGTTAAT GAATCTGGCC
         HBF3                      HB65F2
       ──────▶         ───────────────────────▶
121 ACCTGGGTGG GAAGTAATTT GGAAGACCCA GCATCCAGGG AATTAGTAGT CAGCTATGTC
                                                              HB65F1c
                                                    ◀───────────────
181 AATGTTAATA TGGGCCTAAA AATCAGACAA CTATTGTGGT TCACATTTC CTGCCTTACT
    ─────────                                                HB65R1c
                                                    ───────────────
241 TTTGGAAGAG AAACTGTTTT GGAGTATTTG GTATCTTTTG GAGTGTGGAT TCGCACTCCT
    ───▶
301 CCCGCTTACA GACCACCAAA TGCCCCTATC TTATCAACAC TTCCGGAAAC TACTGTTGTT
            HB65R2                     HBR3
       ◀───────────         ◀───────────────
361 AGACGACGAG GCAGGTCCCC TAGAAGAAGA ACTCCCTCGC CTCGCAGACG AAGGTCTCAA

421 TCGCCGCGTC
```

Fig. 14
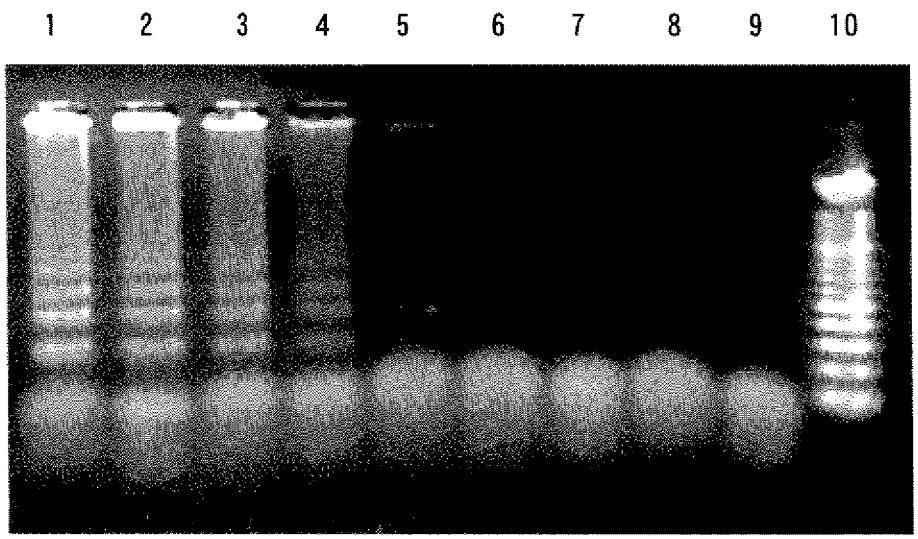
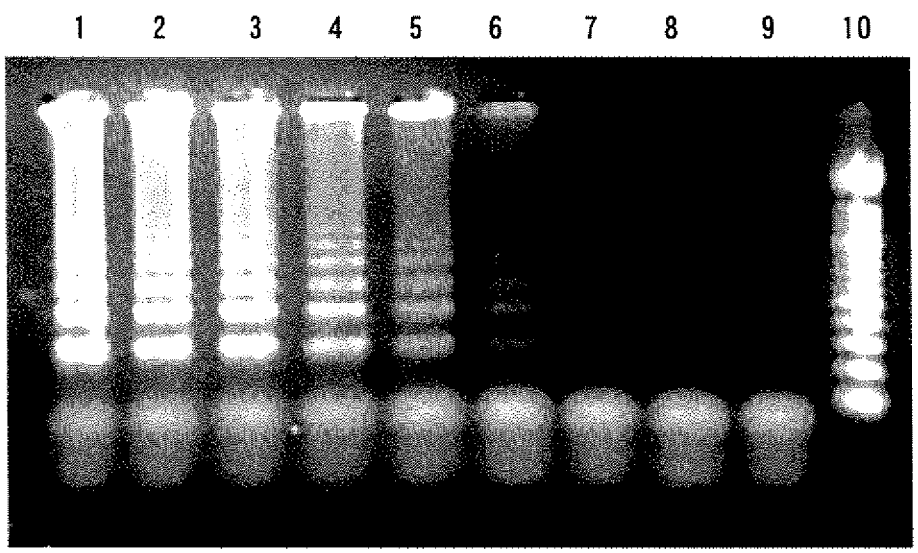

Fig. 15

```
6001 GCGCCCAATA CGCAAACCGC CTCTCCCCGC GCGTTGGCCG ATTCATTAAT GCAGCTGGCA

6061 CGACAGGTTT CCCGACTGGA AAGCGGGCAG TGAGCGCAAC GCAATTAATG TGAGTTAGCT
                                           M13F3                M13F2 d4
6121 CACTCATTAG GCACCCCAGG CTTTACACTT TATGCTTCCG GCTCGTATGT TGTGTGGAAT

6181 TGTGAGCGGA TAACAATTTC ACACAGGAAA CAGCTATGAC CATGATTACG AATTCGAGCT
                  M13F1c d4
6241 CGGTACCCGG GGATCCTCTA GAGTCGACCT GCAGGCATGC AAGCTTGGCA CTGGCCGTCG
                 M13R1c d4          A
6301 TTTTACAACG TCGTGACTGG GAAAACCCTG GCGTTACCCA ACTTAATCGC CTTGCAGCAC
                                M13R2 d4              M13R3
6361 ATCCCCCTTT CGCCAGCTGG CGTAATAGCG AAGAGGCCCG CACCGATCGC CCTTCCCAAC

6421 AGTTGCGCAG CCTGAATGGC GAATGGCGCT TGCCTGGTT TCCGGCACCA GAAGCGGTGC

6481 CGGAAAGCTG GCTGGAGTGC GATCTTCCTG AGGCCGATAC GGTCGTCGTC CCCTCAAACT

6541 GGCAGATGCA CGGTTACGAT GCGCCCATCT ACACCAACGT AACCTATCCC ATTACGGTCA
```

Fig. 17

```
  1 ATTCCGCCGG AGAGCTGTGT CACCATGTGG GTCCCGGTTG TCTTCCTCAC CCTGTCCGTG

61 ACGTGGATTG GTGCTGCACC CCTCATCCTG TCTCGGATTG TGGGAGGCTG GGAGTGCGAG
                                                 PSAF3                    PSAF2
121 AAGCATTCCC AACCCTGGCA GGTGCTTGTG CCTCTCGTG GCAGGGCAGT CTGCGGCGGT
                                                             PSAF1c
181 GTTCTGGTGC ACCCCAGTG GGTCCTCACA GCTGCCCACT GCATCAGGAA CAAAAGCGTG

241 ATCTTGCTGG GTCGGCACAG CCTGTTTCAT CCTGAAGACA CAGGCCAGGT ATTTCAGGTC
     Sau3AI         PSAR1c                                              PSAR2
301 AGCCACAGCT TCCCACACCC GCTCTACGAT ATGAGCCTCC TGAAGAATCG ATTCCTCAGG
                PSAR3

361 CCAGGTGATG ACTCCAGCCA CGACCTCATG CTGCTCCGCC TGTCAGAGCC TGCCGAGCTC

421 ACGGATGCTG TGAAGGTCAT GGACCTGCCC ACCCAGGAGC CAGCACTGGG GACCACCTGC

481 TACGCCTCAG GCTGGGGCAG CATTGAACCA GAGGAGT
```

METHOD OF SYNTHESIZING NUCLEIC ACID

This application is a divisional of U.S. application Ser. No. 10/782,040, filed Feb. 19, 2004 (now U.S. Pat. No. 7,494,790), which is a division of U.S. application Ser. No. 10/132,561, filed Apr. 24, 2002 (now U.S. Pat. No. 6,974,670), which is a continuation of U.S. application Ser. No. 09/530,061, filed Sep. 1, 2000 (now U.S. Pat. No. 6,410,278), which is a national stage application under 35 U.S.C. § 371 from PCT Application No. PCT/JP99/06213, filed Nov. 8, 1999, which claims the priority benefit of Japanese Patent Application No. 10317476, filed Nov. 9, 1998.

TECHNICAL FIELD

The present invention relates to a method of synthesizing nucleic acid composed of a specific nucleotide sequence, which is useful as a method of amplifying nucleic acid.

BACKGROUND ART

An analysis method based on complementarity of a nucleic acid nucleotide sequence can analyze genetic traits directly. Accordingly, this analysis is a very powerful means for identification of genetic diseases, canceration, microorganisms etc. Further, a gene itself is the object of detection, and thus time-consuming and cumbersome procedures such as in culture can be omitted in some cases.

Nevertheless, the detection of a target gene present in a very small amount in a sample is not easy in general so that amplification of a target gene itself or its detection signal is necessary. As a method of amplifying a target gene, the PCR (polymerase chain reaction) method is known (Science, 230, 1350-1354, 1985). Currently, the PCR method is the most popular method as a technique of amplifying nucleic acid in vitro. This method was established firmly as an excellent detection method by virtue of high sensitivity based on the effect of exponential amplification. Further, since the amplification product can be recovered as DNA, this method is applied widely as an important tool supporting genetic engineering techniques such as gene cloning and structural determination. In the PCR method, however, there are the following noted problems: a special temperature controller is necessary for practice; the exponential progress of the amplification reaction causes a problem in quantification; and samples and reaction solutions are easily contaminated from the outside to permit nucleic acid mixed in error to function as a template.

As genomic information is accumulated, analysis of single nucleotide polymorphism (SNPS) comes to attract attention. Detection of SNPs by means of PCR is feasible by designing a primer such that its nucleotide sequence contains SNPs. That is, whether a nucleotide sequence complementary to the primer is present or not can be inferred by determining whether a reaction product is present or not. However, once a complementary chain is synthesized in error in PCR by any chance, this product functions as a template in subsequent reaction, thus causing an erroneous result. In practice, it is said that strict control of PCR is difficult with the difference of only one base given at the terminal of the primer. Accordingly, it is necessary to improve specificity in order to apply PCR to detection of SNPs.

On one hand, a method of synthesizing nucleic acid by a ligase is also practically used. The LCR method (ligase chain reaction, Laffler T G; Garrino J J; Marshall R L; Ann. Biol. Clin. (Paris), 51:9, 821-6, 1993) is based on the reaction in which two adjacent probes are hybridized with a target sequence and ligated to each other by a ligase. The two probes could not be ligated in the absence of the target nucleotide sequence, and thus the presence of the ligated product is indicative of the target nucleotide sequence. Because the LCR method also requires control of temperature for separation of a complementary chain from a template, there arises the same problem as in the PCR method. For LCR, there is also a report on a method of improving specificity by adding the step of providing a gap between adjacent probes and filling the gap by a DNA polymerase. However, what can be expected in this modified method is specificity only, and there still remains a problem in that control of temperature is required. Furthermore, use of the additional enzyme leads to an increase in cost.

A method called the SDA method (strand displacement amplification) [Proc. Natl. Acad. Sci. USA, 89, 392-396, 1992] [Nucleic Acid. Res., 20, 1691-1696, 1992] is also known as a method of amplifying DNA having a sequence complementary to a target sequence as a template. In the SDA method, a special DNA polymerase is used to synthesize a complementary chain starting from a primer complementary to the 3'-side of a certain nucleotide sequence while displacing a double-stranded chain if any at the 5'-side of the sequence. In the present specification, the simple expression "5'-side" or "3'-side" refers to that of a chain serving as a template. Because a double-stranded chain at the 5'-side is displaced by a newly synthesized complementary chain, this technique is called the SDA method. The temperature-changing step essential in the PCR method can be eliminated in the SDA method by previously inserting a restriction enzyme recognition sequence into an annealed sequence as a primer. That, is, a nick generated by a restriction enzyme gives a 3'-OH group acting as the origin of synthesis of complementary chain, and the previously synthesized complementary chain is released as a single-stranded chain by strand displacement synthesis and then utilized again as a template for subsequent synthesis of complementary chain. In this manner, the complicated control of temperature essential in the PCR method is not required in the SDA method.

In the SDA method, however, the restriction enzyme generating a nick should be used in addition to the strand displacement-type DNA polymerase. This requirement for the additional enzyme is a major cause for higher cost. Further, because the restriction enzyme is to be used not for cleavage of both double-stranded chains but for introduction of a nick (that is, cleavage of only one of the chains), a dNTP derivative such as α-thio dNTP should be used as a substrate for synthesis to render the other chain resistant to digestion with the enzyme. Accordingly, the amplification product by SDA has a different structure from that of natural nucleic acid, and there is a limit to cleavage with restriction enzymes or application of the amplification product to gene cloning. In this respect too, there is a major cause for higher cost. In addition, when the SDA method is applied to an unknown sequence, there is the possibility that the same nucleotide sequence as the restriction enzyme recognition sequence used for introducing a nick may be present in a region to be synthesized. In this case, it is possible that a complete complementary chain is prevented from being synthesized.

NASBA (nucleic acid sequence-based amplification, also called the TMA/transcription mediated amplification method) is known as a method of amplifying nucleic acid wherein the complicated control of temperature is not necessary. NASBA is a reaction system wherein DNA is synthesized by DNA polymerase in the presence of target RNA as a template with a probe having a T7 promoter added thereto, and the product is formed with a second probe into a double-stranded chain, followed by transcription by T7 RNA polymerase with the formed double-stranded chain as a template to amplify a large amount of RNA (Nature, 350, 91-92, 1991). NASBA requires some heat denaturation steps until double-stranded DNA is completed, but the subsequent transcriptional reaction by T7 RNA polymerase proceeds under isothermal conditions. However, a combination of plural enzymes such as reverse transcriptase, RNase H, DNA polymerase and T7 RNA polymerase is essential, and this is unfavorable for cost similarly to SDA. Further, because it is complicated to set up conditions for a plurality of enzyme reaction, this method is hardly widespread as a general analytical method. In the known reactions of amplification of nucleic acid, there remain problems such as complicated control of temperature and the necessity for plural enzymes as described above For these known reactions of synthesizing nucleic acid, there are few reports on an attempt for further improving the efficiency of synthesis of nucleic acid without sacrificing specificity or cost. For example, in a method called RCA (rolling-circle amplification), it was shown that single-stranded DNA having a series of nucleotide sequences complementary to a padlock probe can be synthesized continuously in the presence of a target nucleotide sequence (Paul M. Lizardi et al., Nature Genetics, 19, 225-232, July, 1998). In RCA, a padlock probe having a special structure wherein each of the 5'- and 3'-terminals of a single oligonucleotide constitutes an adjacent probe in LCR is utilized. Then, the continuous reaction of synthesizing complementary chain with the padlock probe as a template which was ligated and cyclized in the presence of a target nucleotide sequence is triggered by combination with a polymerase catalyzing the strand displacement-type reaction of synthesizing complementary chain. Single-stranded nucleic acid having a structure of a series of regions each consisting of the same nucleotide sequence is thus formed. A primer is further annealed to this single-stranded nucleic acid to synthesize its complementary chain and a high degree of amplification is thus realized. However, there still remains the problem of the necessity for a plurality of enzymes. Further, triggering of synthesis of complementary chain depends on the reaction of ligating two adjacent regions, and its specificity is basically the same as in LCR.

For the object of supplying 3'-OH, there is a known method in which a nucleotide sequence is provided at the 3'-terminal with a sequence complementary thereto and a hair pin loop is formed at the terminal (Gene, 71, 29-40, 1988). Synthesis of complementary chain with a target sequence itself as a template starts at the hairpin loop to form single-stranded nucleic acid composed of the complementary nucleotide sequence. For example, a structure in which annealing occurs in the same chain at the terminal to which a complementary nucleotide sequence has been linked is realized in PCT/FR95/00891. In this method, however, the step in which the terminal cancels base pairing with the complementary chain and base pairing is constituted again in the same chain is essential. It is estimated that this step proceeds depending on a subtle equilibrium state at the terminal of mutually complementary nucleotide sequences involving base pairing. That is, an equilibrium state maintained between base pairing with a complementary chain and base pairing in the same chain is utilized and the only chain annealing to the nucleotide sequence in the same chain serves as the origin of synthesis of a complementary chain. Accordingly, it is considered that strict reaction conditions should be set to achieve high reaction efficiency. Further, in this prior art, the primer itself forms a loop structure. Accordingly, once a primer dimer is formed, amplification reaction is automatically initiated regardless of whether a target nucleotide sequence is present or not, and an unspecific synthetic product is thus formed. This can be a serious problem. Further, formation of the primer dimer and subsequent consumption of the primer by unspecific synthetic reaction lead to a reduction in the amplification efficiency of the desired reaction.

Besides, there is a report that a region not serving as a template for DNA polymerase was utilized to realize a 3'-terminal structure annealing to the same chain (EP713922). This report also has the same problem as in PCT/FR95/00891 supra in respect of the utilization of dynamic equilibrium at the terminal or the possibility of unspecific synthetic reaction due to formation of a dimer primer. Further, a special region not serving as a template for DNA polymerase should be prepared as a primer.

Further, in various signal amplification reactions to which the principle of NASBA described above is applied, an oligonucleotide having a hairpin structure at the terminal thereof is often utilized to supply a double-stranded promoter region (JP-A 5-211873). However, these techniques are not those permitting, successive supply of 3'-OH for synthesis of a complementary chain. Further, a hairpin loop structure having a 3'-terminal annealed in the same chain is utilized for the purpose of obtaining a DNA template transcribed by RNA polymerase is utilized in JP-A10-510161 (WO96/17079). In this method, the template is amplified by using transcription into RNA and reverse transcription from RNA to DNA. In this method, however, the reaction system cannot be constituted without a combination of a plurality of enzymes.

DISCLOSURE OF THE INVENTION

The object of the present invention is to provide a method of synthesizing nucleic acid based on a novel principle. A more specific object is to provide a method capable of realizing the synthesis of nucleic acid depending on sequence efficiently at low costs. That is, an object of the present invention is to provide a method capable of achieving the synthesis and amplification of nucleic acid by a single enzyme even under isothermal reaction conditions. Another object of the present invention is to provide a method of synthesizing nucleic acid which can realize high specificity difficult to achieve in the known reaction principle of nucleic acid synthesis, as well as a method of amplifying nucleic acid by applying said synthetic method.

The present inventors focused their attention on the fact that the utilization of a polymerase catalyzing strand displacement-type synthesis of complementary chain is useful for nucleic acid synthesis not depending on complicated control of temperature. Such a DNA polymerase is an enzyme utilized in SDA and RCA. However, even if such an enzyme is used, another enzyme reaction is always required for supplying 3'-OH as the origin of synthesis in the known means based on primers, such as SDA.

Under these circumstances, the present inventors examined supply of 3'-OH from a completely different viewpoint from the known approach. As a result, the present inventors found that by utilizing an oligonucleotide having a special structure, 3'-OH can be supplied without any additional enzyme reaction, thereby completing the present invention. That is, the present invention relates to a method of synthesizing nucleic acid, a method of amplifying nucleic acid by applying said method of synthesizing nucleic acid and a novel oligonucleotide enabling said methods, as follows:

1. A method of synthesizing nucleic acid having complementary nucleotide sequences linked alternately in a single-stranded chain, comprising:

a) the step of giving nucleic acid which is provided at the 3'-terminal thereof with a region F1 capable of annealing to a part F1c in the same chain and which upon annealing of the region F1 to F1c, is capable of forming a loop containing a region F2c capable of base pairing, b) the step of performing synthesis of a complementary chain wherein the 3"-terminal of F1 having annealed to F1c serves as the origin of synthesis, c) the step of annealing, to a region F2c, of an oligonucleotide provided with the 3'-terminal thereof with F2 consisting of a sequence complementary to the region F2c, followed by synthesis, with said oligonucleotide as the origin of synthesis, of a complementary chain by a polymerase catalyzing the strand displacement reaction of synthesizing a complementary chain to displace the complementary chain synthesized in step b), and d) the step of annealing, to the complementary chain displaced in step c) to be ready for base pairing, of a polynucleotide provided at the 3'-terminal thereof with a sequence complementary to an arbitrary region in said chain synthesized in step c), followed by synthesis, with said 3'-terminal as the origin of synthesis, of a complementary chain by a polymerase catalyzing the strand displacement reaction of synthesizing a complementary chain to displace the complementary chain synthesized in step c).

2. The method according to item 1, wherein in step d), the origin of synthesis is a region R1 present at the 3'-terminal in the same chain and capable of annealing to a region R1c, and a loop containing the region R2c capable of base pairing is formed by annealing R1 to R1c.

3. An oligonucleotide composed of at least two regions X2 and X1c below, and X1c is linked to the 5'-side of X2, X2: a region having a nucleotide sequence complementary to an arbitrary, region X2c in nucleic acid having a specific nucleotide sequence, and X1c: a region having substantially the same nucleotide sequence as in a region X1c located at the 5"-side of the region X2c in nucleic acid having a specific nucleotide sequence.

4. The method according to item 1, wherein the nucleic acid in step a) is second nucleic acid provided by the following steps i) the step of annealing, to a region F2c in nucleic acid serving as a template, of a region F2 in the oligonucleotide described in item 3 wherein the region X2 is a region F2 and the region X1c is a region F1c, ii) the step of synthesizing first nucleic acid having a nucleotide sequence complementary to the template wherein F2 in the oligonucleotide serves as the origin of synthesis, iii) the step of rendering an arbitrary region in the first nucleic acid synthesized in step ii) ready for base pairing, and iv) the step of annealing an oligonucleotide having a nucleotide sequence complementary to the region made ready for base pairing in the first nucleic acid in step iii), followed by synthesizing second nucleic acid with said oligonucleotide as the origin of synthesis and rendering F1 at the 3'-terminal thereof ready for base pairing.

5. The method according to item 4, wherein the region enabling base pairing in step iii) is R2c, and the oligonucleotide in step iv) is the oligonucleotide described in item 3 wherein the region X2c is a region R2c and the region X1c is a region R1c.

6. The method according to item 4 or 5, wherein the step of rendering base pairing ready in steps iii) and iv) is conducted by the strand displacement synthesis of complementary chain by a polymerase catalyzing the strand displacement reaction of synthesizing complementary chain wherein an outer primer annealing to the 3'-side of F2c in the template and an outer primer annealing to the 3'-side of the region used as the origin of synthesis in step iv) for the first nucleic acid serve as the origin of synthesis.

7. The method according to item 6, wherein the melting temperature of each oligonucleotide and its complementary region in the template used in the reaction is in the following relationship under the same stringency:

(outer primer/region at the 3'-side in the template)≤
(F2c/F2 and R2c/R2)≤(F1c/F1 and R1c/R1).

8. The method according to any one of items 4 to 7, wherein the nucleic acid serving as the template is RNA, and the synthesis of complementary chain in step ii) is conducted by an enzyme having a reverse transcriptase activity.

9. A method of amplifying nucleic acid having complementary nucleotide sequences linked alternately in a single-stranded chain by repeatedly conducting the following steps:

A) the step of providing a template which is provided at the 3'- and 5'-terminals thereof with a region consisting of a nucleotide sequence complementary to each terminal region in the same chain and which upon annealing of these mutually complementary nucleotide sequences, forms a loop capable of base pairing therebetween, B) the step of performing the synthesis of complementary chain wherein the 3'-terminal of said template annealed to the same chain serves as the origin of synthesis, C) the step of annealing, to the loop portion, of an oligonucleotide provided at the 3'-terminal thereof with a complementary nucleotide sequence to a loop which among said loops, is located at the 3'-terminal site, followed by synthesis, with the oligonucleotide as the origin of synthesis, of a complementary chain by a polymerase catalyzing the strand displacement reaction of synthesizing a complementary chain to displace the complementary chain synthesized in step B) to make the 3'-terminal thereof ready for base pairing, and D) the step wherein the chain with the 3'-terminal made ready for base pairing in step C) serves as a new template.

10. The method according to item 9, wherein the oligonucleotide in step C) is provided at the 5'-terminal thereof with a nucleotide sequence complementary to the 3'-terminal serving as the origin of synthesis in step B).

11. The method according to item 10, further comprising the step where a complementary chain synthesized with the oligonucleotide in step C) as the origin of synthesis is used as a template in step A).

12. The method according to item 9, wherein the template in step A) is synthesized by the method described in item 5.

13. The method according to item 1 or 9, wherein the strand displacement reaction of synthesizing complementary chain is carried out in the presence of a melting temperature regulator.

14. The method according to item 13, wherein the melting temperature regulator is betaine.

15. The method according to item 14, wherein 0.2 to 3.0 M betaine is allowed to be present in the reaction solutions 16. A method of detecting a target nucleotide sequence in a sample, which comprises performing an amplification method described in any one of items 9 to 15 and observing whether an amplification reaction product is generated or not.

17. The method according to item 16, wherein a probe containing a nucleotide sequence complementary to the loop is added to the amplification reaction product and hybridization therebetween is observed.

18. The method according to item 17, wherein the probe is labeled on particles and aggregation reaction occurring upon hybridization is observed.

19. The method according to item 16, wherein an amplification method described in any one of items 9 to 15 is conducted in the presence of a detector for nucleic acid, and whether an amplification reaction product is generated or not is observed on the basis of a change in the signal of the detector.

20. A method of detecting a mutation in a target nucleotide sequence by the detection method described in item 16, wherein a mutation in a nucleotide sequence as the subject of amplification prevents synthesis of any one of complementary chains constituting the amplification method.

21. A kit for synthesis of nucleic acid having complementary chains alternately linked in a single-stranded chain, comprising the following elements:

i) the oligonucleotide described in item 3 wherein the region F2c in nucleic acid as a template is X2c, and F1c located at the 5'-side of F2c is X1c;

ii) an oligonucleotide containing a nucleotide sequence complementary to an arbitrary region in a complementary chain synthesized with the oligonucleotide in (i) as a primer;

iii) an oligonucleotide having a nucleotide sequence complementary to a region F3c located at the 3'-side of the region F2c in the nucleic acid serving as a template;

iv) a DNA polymerase catalyzing the strand displacement-type reaction of synthesizing complementary chain; and v) a nucleotide serving as a substrate for the element iv).

22. The kit according to item 21, wherein the oligonucleotide in ii) is the oligonucleotide described in item 3 wherein an arbitrary region R2c in a complementary chain synthesized with the oligonucleotide in i) as the origin of synthesis is X2c, and R1c located at the 5' of R2c is X1c.

23. The kit according to item 22, further comprising:

vi) an oligonucleotide having a nucleotide sequence complementary to a region R3c located at the 3'-side of the arbitrary R2c in a complementary chain synthesized with the oligonucleotide in i) as the origin of synthesis.

24. A kit for detection of a target nucleotide sequence, comprising a detector for detection of a product of nucleic acid synthetic reaction additionally in a kit described in any one of items 21 to 23.

The nucleic acid having complementary nucleotide sequences linked alternately in a single-stranded chain as the object of synthesis in the present invention means nucleic acid having mutually complementary nucleotide sequences linked side by side in a single-stranded chain. Further, in the present invention, it should contain a nucleotide sequence for forming a loop between the complementary chains. In the present invention, this sequence is called the loop-forming sequence. The nucleic acid synthesized by the present invention is composed substantially of mutually complementary chains linked via the loop-forming sequence. In general, a strand not separated into 2 or more molecules upon dissociation of base pairing is called a single-stranded chain regardless of whether it partially involves base pairing or not. The complementary nucleotide sequence can form base pairing in the same chain. An intramolecular base-paired product, which can be obtained by permitting the nucleic acid having complementary nucleotide sequences linked alternately in a single-stranded chain according to the present invention to be base-paired in the same chain, gives a region constituting an apparently double-stranded chain and a loop not involving base pairing.

That is, the nucleic acid having complementary nucleotide sequences linked alternately in a single-stranded chain according to the present invention contains complementary nucleotide sequences capable of annealing in the same chain, and its annealed product can be defined as single-stranded nucleic acid constituting a loop not involving base pairing at a bent hinged portion. A nucleotide having a nucleotide sequence complementary thereto can anneal to the loop not involving base pairing. The loop-forming sequence can be an arbitrary nucleotide sequence. The loop-forming sequence is capable of base pairing so as to initiate the synthesis of a complementary chain for displacement, and is provided preferably with a sequence distinguishable from a nucleotide sequence located in the other region in order to achieve specific annealing. For example, in a preferred embodiment, the loop-forming sequence contains substantially the same nucleotide sequence as a region F2c (or R2c) located at the 3'-side of a region (i.e. F1c or R1c) derived from nucleic acid as a template and annealed in the same chain.

In the present invention, substantially the same nucleotide sequence is defined as follows. That is, when a complementary chain synthesized with a certain sequence as a template anneals to a target nucleotide sequence to give the origin of synthesizing a complementary chain, this certain sequence is substantially the same as the target nucleotide sequence. For example, substantially the same sequence as F2 includes not only absolutely the same nucleotide sequence as F2 but also a nucleotide sequence capable of functioning as a template giving a nucleotide sequence capable of annealing to F2 and acting as the origin of synthesizing complementary chain. The term "anneal" in the present invention means formation of a double-stranded structure of nucleic acid through base pairing based on the law of Watson-Crick. Accordingly, even if a nucleic acid chain constituting base pairing is a single-stranded chain, annealing occurs if intramolecular complementary nucleotide sequences are base-paired. In the present invention, annealing and hybridization have the same meaning in that the nucleic acid constitutes a double-stranded structure through base pairing.

The number of pairs of complementary nucleotide sequences constituting the nucleic acid according to the present invention is at least 1. According to a desired mode of the present invention, it may be 2 or more. In this case, there is theoretically no upper limit to the number of pairs of complementary nucleotide sequences constituting the nucleic acid. When the nucleic acid as the synthetic product of the present invention is constituted of plural sets of complementary nucleotide sequences, this nucleic acid is composed of repeated identical nucleotide sequences.

The nucleic acid having complementary nucleotide sequences linked alternately in a single-stranded chain synthesized by the present invention may not have the same structure as naturally occurring nucleic acid. It is known that if a nucleotide derivative is used as a substrate when nucleic acid is synthesized by the action of a DNA polymerase, a nucleic acid derivative can be synthesized. The nucleotide derivative used includes nucleotides labeled with a radioisotope or nucleotide derivatives labeled with a binding ligand such as biotin or digoxin. These nucleotide derivatives can be used to label nucleic acid derivatives as the product. Alternatively, if fluorescent nucleotides are used as a substrate, the nucleic acid as the product can be a fluorescent derivative. Further, this product may be either DNA or RNA. Which one is formed is determined by a combination of the structure of a primer, the type of a substrate for polymerization and polymerization reagents for carrying out polymerization of nucleic acid.

Synthesis of the nucleic acid having the structure described above can be initiated by use of a DNA polymerase having the strand displacement activity and nucleic acid which is provided at the 3'-terminal thereof with a region F1 capable of annealing to a part F1c in the same chain and which upon annealing of the region F1 to F1c, is capable of forming a loop containing a region F2c capable of base pairing. There are many reports on the reaction of synthesizing complementary chain wherein a hairpin loop is formed and a sample sequence itself is used as a template, while in the present invention the portion of the hairpin loop is provided with a region capable of base pairing, and there is a novel feature on utilization of this region in synthesizing complementary chain. By use of this region as the origin of synthesis, a complementary chain previously synthesized with a sample sequence itself as a template is displaced. Then, a region R1c (arbitrary region) located at the 3'-terminal of the displaced chain is in a state ready for base-pairing. A region having a complementary sequence to this R1c is annealed thereto, resulting in formation of the nucleic acid (2 molecules) having a nucleotide sequence extending from F1 to R1c and its complementary chain linked alternately via the loop-forming sequence. In the present invention; the arbitrary region such as R1c above can be selected arbitrarily provided that it can be annealed to a polynucleotide having a nucleotide sequence complementary to that region, and that a complementary chain synthesized with the polynucleotide as the origin of synthesis has necessary functions for the present invention.

In the present invention, the term "nucleic acid" is used. The nucleic acid in the present invention generally includes both DNA and RNA. However, nucleic acid whose nucleotide is replaced by an artificial derivative or modified nucleic acid from natural DNA or RNA is also included in the nucleic acid of the present invention insofar as it functions as a template for synthesis of complementary chain. The nucleic acid of the present invention is generally contained in a biological sample. The biological sample includes animal, plant or microbial tissues, cells, cultures and excretions, or extracts therefrom. The biological sample of the present invention includes intracellular parasitic genomic DNA or RNA such as virus or mycoplasma. The nucleic acid of the present invention may be derived from nucleic acid contained in said biological sample. For example, cDNA synthesized from mRNA, or nucleic acid amplified on the basis of nucleic acid derived from the biological sample, is a typical example of the nucleic acid of the present invention.

The nucleic acid characteristic of the present invention which is provided at the 3'-terminal thereof with a region F1 capable of annealing to a part F1c in the same chain and which upon annealing of the region F1 to F1c, is capable of forming a loop containing a region F2c capable of base pairing can be obtained in various methods. In the most preferable embodiment, the reaction of synthesizing complementary chain utilizing an oligonucleotide having the following structure can be used to give the structure.

That is, the useful oligonucleotide in the present invention consists of at least two regions X2 and X1c below wherein X1c is ligated to the 5'-side of X2.

X2: a region having a nucleotide sequence complementary to a region X2c in nucleic acid having a specific nucleotide sequence.

X1c: a region having substantially the same nucleotide sequence as a region X1c located at the 5'-side of the region X2c in nucleic acid having a specific nucleotide sequence.

Here, the nucleic acid having a specific nucleotide sequence by which the structure of the oligonucleotide of the invention is determined refers to nucleic acid serving as a template when the oligonucleotide of the present invention is used as a primer. In the case of detection of nucleic acid based on the synthetic method of the present invention, the nucleic acid having a specific nucleotide sequence is a detection target or nucleic acid derived from the detection target. The nucleic acid having a specific nucleotide sequence refers to nucleic acid wherein at least a part of the nucleotide sequence is revealed or predictable. The part of the nucleotide sequence revealed is the region X2c and the region X1c located at the 5'-side thereof. It can be supposed that these 2 regions are contiguous or located apart from each other. By the relative positional relationship of the two, the state of a loop formed upon self-annealing of nucleic acid as the product is determined. The distance between the two is preferably not very apart from each other in order that nucleic acid as the product is subjected to self-annealing preferentially over intermolecular annealing. Accordingly, the positional relationship of the two is preferably that they are contiguous via a distance of usually 0 to 100 bases. However, in the formation of a loop by self-annealing described below, there can be the case where it would be disadvantageous for formation of a loop in a desired state that the two are too close to each other. In the loop, there is a need for a structure for annealing of a new oligonucleotide and for readily initiating the strand-displacement reaction of synthesizing a complementary chain with said oligonucleotide as the origin of synthesis. More preferably, the distance between the region X2c and the region X1c located at the 5'-side of X2c is designed to be 0 to 100 bases, more desirably 10 to 70 bases. This numerical value shows a length excluding X1c and X2. The number of bases constituting the part of a loop is that of this length plus a region corresponding to X2.

Both the terms "same" and "complementary" used for characterization of the nucleotide sequence constituting the oligonucleotide based on the present invention do not mean being absolutely the same or absolutely complementary. That is, the same sequence as a certain sequence includes sequences complementary to nucleotide sequences capable of annealing to a certain sequence. On the other hand, the complementary sequence means a sequence capable of annealing under stringent conditions to provide a 3'-terminal serving as the origin of synthesis of complementary chain.

Usually, the regions X2 and X1c constituting the oligonucleotide of the present invention for the nucleic acid having a specific nucleotide sequence are located contiguously without being overlapped. If there is a common part in both the nucleotide sequences, the two can be partially overlaid. Because X2 should function as a primer, it should always be a 3'-terminal. On the other hand, X1c should give the function of a primer as described blow to the 3'-terminal of a complementary chain synthesized with the nucleic acid as a template, and thus it shall be arranged at the 5'-terminal. The complementary chain obtained with this oligonucleotide as the origin of synthesis serves as a template for synthesis of complementary chain in the reverse direction in the next step, and finally the part of the oligonucleotide of the present invention is copied as a template into a complementary chain. The 3'-terminal generated by copying has the nucleotide sequence X1, which anneals to X1c in the same chain to form a loop.

In the present invention, the oligonucleotide means the one that satisfies the 2 requirements, that is, it must be able to form complementary base pairing and give an —OH group serving as the origin of synthesis of complementary chain at the 3'-terminal. Accordingly, its backbone is not necessarily limited to the one via phosphodiester linkages. For example, it may be composed of a phosphothioate derivative having S in place of P as a backbone or a peptide nucleic acid based on peptide linkages. The bases may be those capable of complementary base pairing. In the nature, there are 5 bases, that is, A, C, T, G and U, but the base can be an analogue such as bromodeoxyuridine. The oligonucleotide used in the present invention functions preferably not only as the origin of synthesis but also as a template for synthesis of complementary chain. The term polynucleotide in the present invention includes oligonucleotides. The term "polynucleotide" is used in the case where the chain length is not limited, while the term "oligonucleotide" is used to refer to a nucleotide polymer having a relatively short chain length.

The oligonucleotide according to the present invention has such a chain length as to be capable of base pairing with a complementary chain and to maintain necessary specificity under the given environment in the various reactions of synthesizing nucleic acid described below. Specifically, it is composed of 5 to 200 base pairs, more preferably 10 to 50 base pairs. The chain length of a primer recognizing the known polymerase catalyzing the sequence-dependent nucleic acid synthetic reaction is at least about 5 bases, so the chain length of the annealing part should be longer than that. In addition, a length of 10 bases or more is desired statistically in order to expect specificity as the nucleotide sequence. On the other hand, preparation of a too long nucleotide sequence by chemical synthesis is difficult, and thus the chain length described above is exemplified as a desired range. The chain length exemplified here refers to the chain length of a part annealing to a complementary chain. As described below, the oligonucleotide according to the present invention can anneal finally to at least 2 regions individually. Accordingly, it should be understood that the chain length exemplified here is the chain length of each region constituting the oligonucleotide.

Further, the oligonucleotide according to the present invention can be labeled with a known labeling substance. The labeling substance includes binding ligands such as digoxin and biotin, enzymes, fluorescent substances and luminescent substances, and radioisotopes. The techniques of replacing a base constituting an oligonucleotide by a fluorescent analogue are also known (WO95/05391, Proc. Natl. Acad. Sci. USA, 91, 6644-6648, 1994).

Other oligonucleotides according to the present invention can also have been bound to a solid phase. Alternatively, an arbitrary part of the oligonucleotide may be labeled with a binding ligand such as biotin, and it can be immobilized indirectly via a binding partner such as immobilized avidin. When the immobilized oligonucleotide is used as the origin of synthesis, nucleic acid as the synthetic reaction product is captured by the solid phase, thus facilitating its separation. The separated product can be detected by a nucleic acid-specific indicator or by hybridization with a labeling probe. The target nucleic acid fragments can also be recovered by digesting the product with arbitrary restriction enzymes.

The term "template" used in the present invention means nucleic acid serving as a template for synthesizing a complementary chain. A complementary chain having a nucleotide sequence complementary to the template has a meaning as a chain corresponding to the template, but the relationship between the two is merely relative. That is, a chain synthesized as the complementary chain can function again as a template. That is, the complementary chain can become a template.

The oligonucleotide useful in the present invention is not limited to the 2 regions described above and can contain an additional region. While X2 and X1c are arranged at the 3'- and 5'-terminals respectively, an arbitrary sequence can be interposed therebetween. For example, it can be a restriction enzyme recognition site, a promoter recognized by RNA polymerase, or DNA coding for ribozyme. By using it as a restriction enzyme recognition sequence, the nucleic acid having a complementary sequence alternately linked in a single-stranded chain as the synthetic product of the present invention can be cleaved into double-stranded nucleic acids of the same length. By arranging a promoter sequence recognized by RNA polymerase, the synthetic product of the present invention serves as the template to permit further transcription into RNA. By further arranging DNA coding for ribozyme, a system where the transcriptional product is self-cleaved is realized. These additional nucleotide sequences are those functioning after formed into a double-stranded chain. Accordingly, when the single-stranded nucleic acid according to the present invention has formed a loop, these sequences do not function. They do not function until the nucleic acid is elongated and annealed in the absence of a loop to a chain having a complementary nucleotide sequence.

When a promoter is combined with the oligonucleotide based on the present invention in such a direction as to permit transcription of the synthesized region, the reaction product based on the present invention where the same nucleotide sequence is repeated realizes a highly efficient transcriptional system. By combining this system with a suitable expression system, translation into a protein is also feasible. That is, the system can be utilized for transcription and translation into protein in bacteria or animal cells or in vitro.

The oligonucleotide of the present invention having the structure described above can be chemically synthesized. Alternatively, natural nucleic acid may be cleaved with e.g. restriction enzymes and modified so as to be composed of, or ligated into, the nucleotide sequence described above.

The basic principle of the reaction for performing synthesis by utilizing the useful oligonucleotide described above in combination with DNA polymerase having the strand displacement activity in the reaction of synthesizing nucleic acid according to the present invention is described by reference to FIGS. 5 to 6. The oligonucleotide described above (FA in FIG. 5) anneals at X2 (corresponding to F2) to nucleic acid as a template, to provide the origin of synthesis of complementary chain. In FIG. 5, a complementary chain synthesized from FA as the origin of synthesis is displaced by synthesis of complementary chain (described below) from an outer primer (F3), to form a single-stranded chain (FIG. 5-A). When synthesis of complementary chain to the resulting complementary chain is further conducted, the 3'-terminal of nucleic acid synthesized as complementary chain in FIG. 5-A has a nucleotide sequence complementary to the oligonucleotide of the present invention. That is, because the 5'-terminal of the oligonucleotide of the present invention has the same sequence as a region X1c (corresponding to F1c), the 3'-terminal of the nucleic acid thus synthesized has a complementary sequence X1 (F1). FIG. 5 shows that the complementary chain synthesized from R1 as the origin of synthesis is displaced by synthesis of complementary chain by primer R3 as the origin of synthesis. Once the 3'-terminal portion is made ready for base pairing by this displacement, X1 (F1) at the 3'-terminal anneals to X1c (F1c) in the same chain, and elongation reaction with itself as a template proceeds (FIG. 5-B). Then, X2c (F2c) located at the 3'-terminal thereof is left as a loop not involving base pairing. X2 (F2) in the oligonucleotide according to the present invention anneals to this loop, and a complementary chain is synthesized with said oligonucleotide as the origin of synthesis (FIG. 5-B). A product of complementary chain synthetic reaction with the previously synthesized product as a template is displaced by the strand displacement reaction so that it is made ready for base pairing.

By the basic constitution using one kind of oligonucleotide according to the present invention and an arbitrary reverse primer capable of conducting nucleic acid synthesis where a complementary chain synthesized with said oligonucleotide as a primer is used as a template, a plurality of nucleic acid synthetic products as shown in FIG. 6 can be obtained. As can be seen from FIG. 6, (D) is the desired nucleic acid product of the invention having complementary nucleotide sequence alternately linked in a single-stranded chain. Once converted into a single-stranded chain by treatment such as heat denaturation, the other product (E) serves again as a template for forming (D). If the product (D) as nucleic acid in the form of a double-stranded chain is converted into a single-stranded chain by heat denaturation, annealing occurs within the same chain at high probability without forming the original double-stranded chain. This is because a complementary chain having the same melting temperature (Tm) undergoes intramolecular reaction preferentially over intermolecular reaction. Each single-stranded chain derived from the product (D) annealed in the same chain is annealed in the same chain and returned to the state of (B), and each chain further gives one molecule of (D) and (E) respectively. By repeating these steps, it is possible to successively synthesize the nucleic acid having complementary nucleotide sequences linked alternately in a single-stranded chain. The template and the product formed in 1 cycle are increased exponentially, thus making the reaction very efficient.

To realize the state of FIG. 5(A), the initially synthesized complementary chain should, in at least the portion to which the reverse primer anneals, should be ready for base pairing. This step can be achieved by an arbitrary method. That is, an outer primer (F3), which anneals to the first template at a region F3c at the 3'-side of the region F2c to which the oligonucleotide of the present invention anneals, is separately prepared. If this outer primer is used as the origin synthesis to synthesize a complementary chain by a polymerase catalyzing the strand displacement-type synthesis of complementary chain, the complementary chain synthesized from the F2c as the origin of synthesis in the invention is displaced, and as a result the region R1c to be annealed by R1 is made ready for base pairing (FIG. 5). By utilization of the strand displacement reaction, the reaction up to now can proceed under isothermal conditions.

When an outer primer is used, synthesis from the outer primer (F3) should be initiated after synthesis from F2c. In the most simple method, the concentration of the inner primer is made higher than the concentration of the outer primer. Specifically, the primers are used at usually 2- to 50-fold, preferably 4- to 10-fold different concentrations whereby the reaction can proceed as expected. Further, the melting temperature (Tm) of the outer primer is set to be lower than the Tm of the X1 (corresponding to F1 and R1) in the inner primer whereby the timing of synthesis can be controlled. That is, (outer primer F3:F3c)≤F2c/F2)≤(F1c/F1) or (outer primer/region at the 3'-side in the template)≤(X2c:X2)≤(X1c:X1). Here, the reason for (F2c/F2)≤(F1c/F1) is for annealing between F1c/F1 prior to annealing of F2 to the loop. The annealing between F1c/F1 is an intramolecular reaction and may thus proceed preferentially at high probability. However, it is meaningful to consider Tm in order to give more desired reaction conditions. As a matter of course, similar conditions should be considered even in the design of a reverse primer. By using such a relationship, statistically ideal reaction conditions can be achieved. If other conditions are fixed, melting temperature (Tm) can be theoretically calculated by a combination of the length of an annealing complementary chain and bases constituting base-pairing. Accordingly, those skilled in the art can derive preferable conditions on the basis of the disclosure of this specification.

Further, the phenomenon called contiguous stacking can also be applied for controlling timing of annealing of the outer primer. Contiguous stacking is a phenomenon in which an oligonucleotide not capable of annealing independently is made capable of annealing upon being contiguous to the part of a double-stranded chain (Chiara Borghesi-Nicoletti et al., Bio Techniques, 12, 474-477 (1992)). That is, the outer primer is designed so as to be contiguous to F2c (X2c) and not to be able to anneal independently. By doing so, annealing of the outer primer does not occur until F2c (X2c) anneals, and thus the annealing of F2c (X2c) occurs preferentially. On the basis of this principle, the Examples show setting of the nucleotide sequence of an oligonucleotide necessary as a primer for a series of reactions. This step can also be achieved by denaturation under heating or with a DNA helicase.

If the template nucleic acid having F2c (X2c) is RNA, the state of FIG. 5-(A) can also be realized by a different method. For example, if this RNA chain is decomposed, R1 is made ready for base pairing. That is, F2 is annealed to F2c in RNA and a complementary chain is synthesized as DNA by a reverse transcriptase. The RNA serving as a template is decomposed by alkali denaturation or by enzymatic treatment with a ribonuclease acting on RNA in a double-stranded chain of DNA/RNA whereby the DNA synthesized from F2 is formed into a single-stranded chain. For the enzyme selectively decomposing RNA in a double-stranded chain of DNA/RNA, the ribonuclease activity of RNase H or some reverse transcriptases can be utilized. In this manner, the reverse primer can be annealed to R1c made capable of base pairing. Accordingly, the outer primer for rendering R1c ready for base pairing becomes unnecessary.

Alternatively, the strand displacement activity of reverse transcriptase can be utilized for the strand displacement by an outer primer as described above. In this case, a reaction system can be constituted by a reverse transcriptase only. That is, using RNA as a template, it is made possible by a reverse transcriptase to synthesize a complementary chain from F2 annealing to F2c in the template and to synthesize a complementary chain from the outer primer F3 as the origin of synthesis annealing to F3c located at the 3'-side of F2c and to simultaneously displace the previously synthesized complementary chain. When the reverse transcriptase performs the reaction of synthesizing a complementary chain with DNA as the template, all the reactions of synthesizing complementary chains including the synthesis of a complementary chain with R1 as the origin of synthesis annealing to R1c in the displaced complementary chain as the template, the synthesis of a complementary chain with R3 as the origin of synthesis annealing to R3c located at the 3'-side of R1c and the simultaneous displacement reaction, proceed by the reverse transcriptase. If it is not possible to expect that the reverse transcriptase exhibits the DNA/RNA strand displacement activity under given reaction conditions, a DNA polymerase having the strand displacement activity described above may be combined. The mode of obtaining a first single-stranded nucleic acid with RNA as a template as described above constitutes a preferable mode of the present invention. On the other hands, if a DNA polymerase such as Bca DNA polymerase having both strand displacement activity and reverse transcriptase activity is used, not only synthesis of a first single-stranded nucleic acid from RNA but also subsequent reaction with DNA as a template can proceed similarly by the same enzyme.

The reaction system described above brings about various variations inherent in the present invention by utilization of the reverse primer having a specific structure. The most effective variation is described below. That is, the oligonucleotide constituted as described in [5] is used as the reverse primer in the most advantageous mode of the present invention. The oligonucleotide in [5] is an oligonucleotide wherein arbitrary regions R2c and R1c in a complementary chain synthesized with F2 as a primer are X2c and X1c respectively. By use of such a reverse primer, a series of reactions for forming a loop and for synthesizing and displacing a complementary chain from this loop occur in both the sense and antisense chains (forward side and reverse side). As a result, the reaction efficiency for synthesis of the nucleic acid having complementary nucleotide sequences linked alternately in a single-stranded chain according to the present invention is greatly improved while a series of these reactions are feasible under isothermal conditions. Hereinafter, this mode is described in more detail by reference to FIGS. 1 to 3 where this mode is summarized.

In the following mode, 2 kinds of oligonucleotides based on the present invention are prepared. For explanation, these are designated FA and RA. The regions constituting FA and RA are as follows:

|    | X2 | X1c |
|----|----|-----|
| FA | F2 | F1c |
| RA | R2 | R1c |

Here, F2 is a complementary nucleotide sequence to a region F2c in nucleic acid as the template. R2 is a nucleotide sequence complementary to an arbitrary region R2c contained in a complementary chain synthesized with F2 as a primer. F1c and R1c are arbitrary nucleotide sequences located downward from F2c and R2c respectively. The distance between F2 and R2 may be arbitrary. Even if its length is about 1 kbp, sufficient synthesis is feasible under suitable conditions, though depending on the synthetic ability of DNA polymerase to perform the synthesis of a complementary chain. Specifically, when Bst DNA polymerase is used, the desired product is certainly synthesized if the distance between F2 and R2c is 800 bp, preferably 500 bp or less. In PCR involving temperature cycle, the reduction in the enzyme activity by the stress of temperature change is considered to reduce the efficiency of synthesis of a long nucleotide sequence. In a preferable mode of the present invention, the temperature cycle in the step of amplifying nucleic acid is not required, and thus the synthesis and amplification of an even long nucleotide sequence can be certainly achieved.

First, F2 in FA is annealed to nucleic acid as a template and used as the origin of synthesis of a complementary chain. The subsequent reaction steps until FIG. 1(4) are the same as in the previously described basic mode (FIG. 5) in the present invention. The sequence annealed as F3 in FIG. 1(2) is the outer primer described above. A DNA polymerase for conducting the strand displacement-type synthesis of a complementary chain with this primer as the origin of synthesis is used so that the complementary chain synthesized from FA is displaced and made ready for base pairing.

When R2c is made ready for base pairing in (4), RA as a reverse primer anneals thereto in the combination of R2c/R2. Synthesis of a complementary chain with this site as the origin of synthesis proceeds until the chain reaches F1c at the 5'-terminal of FA. Following this reaction of synthesizing a complementary chain, the outer primer R3 for displacement anneals thereto to synthesize a complementary chain, during which strand displacement also proceeds so that the complementary chain synthesized from RA as the origin of synthesis is displaced. In the complementary chain thus displaced, RA is located at the 5'-side thereof and a sequence complementary to FA is located at the 3'-terminal thereof.

At the 3'-side of the single-stranded nucleic acid thus displaced, there is a sequence F1 complementary to F1c in the same chain. F1 rapidly anneals to F1c in the same molecule to initiate synthesis of a complementary chain. When the 3'-terminal (F1) anneals to F1c in the same chain, a loop containing F2c (i.e., a first loop) is formed. (As illustrated in FIG. 2-(7), the same single-stranded nucleic acid also contains at the 5'-side a sequence R1 complementary to R1c in the same chain, which can likewise anneal to form a loop containing R2, i.e., a second loop.) As is also evident from FIG. 2-(7), the part of this loop containing F2c remains ready for base pairing. The oligonucleotide FA of the invention having a nucleotide sequence complementary to F2c anneals to the part of this loop (i.e., the first loop) and acts as the origin of synthesis of a complementary chain (7). Synthesis of a complementary chain from the loop proceeds while the reaction product in the previously initiated complementary chain synthesis from F1 is displaced. As a result, the complementary chain synthesized with itself as the template is made ready for base pairing again at the 3'-terminal. This 3'-terminal is provided with a region R1 capable of annealing to R1c in the same chain, and the two are annealed preferentially due to the rapid intramolecular reaction (i.e. r forming a third loop). The same reaction as the above-described reaction starting from the 3'-terminal synthesized with FA as a template proceeds in this region as well. As a result, the nucleic acid having complementary nucleotide sequences linked alternately in the same single-stranded chain according to the present invention is continued to be extended from R1 as the starting point at the 3'-terminal by successive synthesis of a complementary chain and subsequent displacement thereof. Because R2c is always contained in the loop formed by intramolecular annealing of the 3'-terminal R1, the oligonucleotide (RA) provided with R2 anneals to the loop at the 3'-terminal in the subsequent reaction.

When attention is paid to nucleic acid synthesized as complementary chain from the oligonucleotide annealing to the loop in the single-stranded nucleic acid elongated with itself as the template, synthesis of the nucleic acid having complementary nucleotide sequences linked alternately in the same single-stranded chain according to the present invention also proceeds here. That is, synthesis of a complementary chain from the loop (i.e., the first loop) is completed when it reached RA in e.g. FIG. 2-(7). Then, when the nucleic acid displaced by this nucleic acid synthesis (i.e., forming the third loop) initiates synthesis of complementary chain (FIG. 3-(8)), the reaction reaches the loop which was once the origin of synthesis (i.e., the first loop), and displacement is initiated again. In this manner, the nucleic acid initiated to be synthesized from the loop is also displaced, and as a result, the 3'-terminal R1 capable of annealing in the same chain is obtained (FIG. 3-(10)). This 3'-terminal R1 anneals to R1c in the same chain to initiate synthesis of complementary chain. This reaction is the same as in FIG. 2-(7) except that F is used in place of R. Accordingly, the structure shown in FIG. 3-(10) can function as a new nucleic acid which continues self-elongation and new nucleic acid formation.

The reaction of synthesizing nucleic acid, initiated from the nucleic acid shown in FIG. 3-(10), causes elongation from the 3'-terminal F1 as the origin of synthesis, as opposed to the reaction described above. That is, in the present invention, as one nucleic acid is elongated, the reaction of continuing to supply a new nucleic acid initiating elongation separately proceeds. Further, as the chain is elongated, a plurality of loop-forming sequences are brought about not only at the terminal but also in the same chain. When these loop-forming sequences are made ready for base pairing by the strand displacement synthetic reaction, an oligonucleotide anneals thereto to serve as a base for the reaction of forming a new nucleic acid. Further efficient amplification is achieved by the synthetic reaction starting not only at the terminal but also in the chain. The oligonucleotide RA based on the present invention is combined as the reverse primer as described above whereby elongation and subsequent formation of a new nucleic acid occur. Further, in the present invention, this newly formed nucleic acid itself is elongated and brings about subsequent formation of a new nucleic acid. A series of these reactions continue theoretically permanently to achieve very efficient amplification of nucleic acid. In addition, the reaction in the present invention can be conducted under isothermal conditions.

The reaction products thus accumulated possess a structure having a nucleotide sequence between F1 and R1 and its complementary sequence linked alternately therein. However, both the terminals of the repeating unit have a region consisting of the successive nucleotide sequences F2-F1 (F2c-F1c) and R2-R1 (R2c-R1c). For example, in FIG. 3-(9), the sequences (R2-F2d)-(F1-R2c)-(R1-F1c)-(F2-R2c) are linked in this order from the 5'-side. This is because the amplification reaction based on the present invention proceeds on the principle that the reaction is initiated from F2 (or R2) with an oligonucleotide as the origin of synthesis and then a complementary chain is elongated by the synthetic reaction from F1 (or R1) with the 3'-terminal as the origin of synthesis.

Here, in the most preferable mode, oligonucleotides FA and RA according to the present invention were used as oligonucleotides annealing to the part of a loop. However, even if these oligonucleotide having a limited structure are not used, the amplification reaction according to the present invention can be carried out by use of an oligonucleotide capable of initiating the synthesis of a complementary chain from the loop. That is, the elongating 3'-terminal, once displaced by a complementary chain synthesized from the loop, gives the part of a loop again. Because the nucleic acid having complementary nucleotide sequences linked alternately in a single-stranded chain is always used as a template in the complementary chain synthesis starting from the loop, it is evident that the nucleic acid desired in the present invention can be synthesized. However, the nucleic acid thus synthesized performs synthesis of a complementary chain by forming a loop after displacement, but there is no 3'-terminal available for subsequent formation of a loop, and thus it cannot function as a new template. Accordingly, the product in this case, unlike nucleic acid initiated to be synthesized by FA or RA, cannot be expected to be exponentially amplified. From this reason, an oligonucleotide having the structure of FA or RA is useful for highly efficient synthesis of nucleic acid based on the present invention.

A series of these reactions proceed by adding the following components to single-stranded nucleic acid as a template and then incubating the mixture at such a temperature that the nucleotide sequence constituting FA and RA can form stable base pairing with its complementary nucleotide sequence while the enzyme activity can be maintained.

4 kinds of oligonucleotides:
FA,
RA,
outer primer F3, and
outer primer R3,
DNA polymerase for performing the strand displacement-type synthesis of complementary chain,
an oligonucleotide serving as a substrate for DNA polymerase.

Accordingly, temperature cycle such as in PCR is not necessary. The stable base pairing referred to herein means a state in which at least a part of an oligonucleotide present in the reaction system can give the origin of synthesis of complementary chain. For example, the desired condition for bringing about stable base pairing is to set lower than melting temperature (Tm). Generally, melting temperature (Tm) is regarded as the temperature at which 50% of nucleic acids having mutually complementary nucleotide sequences are base-paired. Setting at melting temperature (Tm) or less is not an essential condition in the present invention, but is one of the reaction conditions to be considered for attaining high efficiency of synthesis. If nucleic acid to be used as a template is a double-stranded chain, the nucleic acid should, in at least a region to which the oligonucleotide anneals, be made ready for base pairing. For this, heat denaturation is generally conducted, and this may be conducted only once as pretreatment before the reaction is initiated.

This reaction is conducted in the presence of a buffer giving suitable pH to the enzyme reaction, salts necessary for annealing or for maintaining the catalytic activity of the enzyme, a protective agent for the enzyme, and as necessary a regulator for melting temperature (Tm). As the buffer, e.g. Tris-HCl having a buffering action in a neutral to weakly alkaline range is used. The pH is adjusted depending on the DNA polymerase used. As the salts, KCl, NaCl, $(NH_4)_2SO_4$ etc. are suitably added to maintain the activity of the enzyme and to regulate the melting temperature (Tm) of nucleic acid. The protective agent for the enzyme makes use of bovine serum albumin or sugars. Further, dimethyl sulfoxide (DMSO) or formamide is generally used as the regulator for melting temperature (Tm). By use of the regulator for melting temperature (Tm), annealing of the oligonucleotide can be regulated under limited temperature conditions. Further, betaine (N,N,N-trimethylglycine) or a tetraalkyl ammonium salt is also effective for improving the efficiency of strand displacement by virtue of its isostabilization. By adding betaine in an amount of 0.2 to 3-0 M, preferably 0.5 to 1.5 M to the reaction solution, its promoting action on the nucleic acid amplification of the present invention can be expected. Because these regulators for melting temperature act for lowering melting temperature, those conditions giving suitable stringency and reactivity are empirically determined in consideration of the concentration of salts, reaction temperature etc.

An important feature in the present invention is that a series of reactions do not proceed unless the positional relationship of a plurality of regions is maintained. By this feature, unspecific synthetic reaction accompanied by unspecific synthesis of complementary chain is effectively prevented. That is, even if a certain unspecific reaction occurs, the possibility for the product to serve as a starting material in the subsequent amplification step is minimized. Further, the regulation of the progress of reactions by many regions brings about the possibility that a detection system capable of strict identification of the desired product in analogous nucleotide sequences can be arbitrarily constituted.

This feature can be utilized for detection of mutations in a gene. In the mode of the invention where the outer primer is used, 4 primers, that is, 2 outer primers and 2 primers consisting of the oligonucleotides of the present invention, are used. That is, unless the 6 regions contained in the 4 oligonucleotides work as designed, the synthetic reaction of the present invention do not proceed. In particular, the sequences of the 3'-terminal of each oligonucleotide as the origin of synthesis of complementary chain and of the 5'-terminal of the X1c region where the complementary chain serves as the origin of synthesis are important. Hence, these important sequences is designed so as to correspond to a mutation to be detected, and the synthetic reaction product of the present invention is observed whereby the presence or absence of a mutation such as base deletion or insertion, or genetic polymorphism such as SNPs can be comprehensively analyzed. Specifically, bases estimated to have a mutation or polymorphism are designed so as to correspond to the vicinity of the 3'-terminal of an oligonucleotide as the origin of synthesis of complementary chain, or of 5'-terminal thereof when a complementary chain is the origin of synthesis. If a mismatch is present at the 3'-terminal as the origin of synthesis of complementary chain or in its vicinity, the reaction of synthesizing a complementary chain to nucleic acid is significantly inhibited. In the present invention, a high degree of amplification reaction is not achieved unless the structure of the terminals of a product in the initial reaction brings about repeated reactions. Accordingly, even if erroneous synthesis occurs, complementary chain synthesis constituting amplification reaction is always interrupted in some of the steps, and thus a high degree of amplification reaction does not occur in the presence of a mismatch. As a result, the mismatch effectively inhibits amplification reaction, and an accurate result is finally brought about. That is, it can be said that the amplification reaction of nucleic acid based on the present invention has a highly completed mechanism for checking the nucleotide sequence. These features are an advantage hardly expectable in e.g. the PCR method where amplification reaction is performed in mere 2 regions.

The region X1c characterizing the oligonucleotide used in the present invention can serve as the origin of synthesis after a complementary sequence is synthesized, and this complementary sequence anneals to the sequence X1 in the same newly synthesized chain whereby synthetic reaction with itself as a template proceeds. Therefore, even if the so-called primer dimer which is often problematic in the prior art is formed, this oligonucleotide does not form a loop. Accordingly, unspecific amplification attributable to the primer dimer cannot occur theoretically, and thus the present oligonucleotide contributes to an improvement in the specificity of the reaction.

Further, according to the present invention, the outer primers shown as F3 (FIG. 1-(2)) or R3 (FIG. 2-(5)) are combined whereby a series of the reactions described above can be conducted under isothermal conditions. That is, the present invention provides a method of amplifying nucleic acid having complementary sequences linked alternately in a single-stranded chain, which comprises the steps shown in item 9 above. In this method, temperature conditions where stable annealing occurs between F2c/F2, between R2c/R2, between F1c/F1, and between R1c/R1 are selected, and preferably F3c/F3 and R3c/R3 are set up to be annealed by the phenomenon of contiguous stacking facilitated by annealing of F2c/F2 and R2c/R2, respectively.

In the present invention, the terms "synthesis" and "amplification" of nucleic acid are used. The synthesis of nucleic acid in the present invention means the elongation of nucleic acid from an oligonucleotide serving as the origin of synthesis. If not only this synthesis but also the formation of other nucleic acid and the elongation reaction of this formed nucleic acid occur continuously, a series of these reactions is comprehensively called amplification.

The single-stranded nucleic acid which is provided at the 3'-terminal thereof with a region F1 capable of annealing to a part F1c in the same chain and which upon annealing of the region F1 to F1c in the same chain, is capable of forming a loop containing a region F2c capable of base pairing is an important element of the present invention. Such a single-stranded nucleic acid can also be supplied on the following principle. That is, the synthesis of a complementary chain is allowed to proceed on the basis of a primer having the following structure. 5'-[region X1 annealing to region X1c located in primer]-[loop forming sequence ready for base pairing]-[region X1c]-[region having a sequence complementary to a template]-3'

As the region having a sequence complementary to a templates two nucleotide sequences, that is, a nucleotide sequence (primer FA) complementary to F1 and a nucleotide sequence (primer RA) complementary to R1c, are prepared. The nucleotide sequence constituting nucleic acid to be synthesized contains a nucleotide sequence extending from the region F1 to the region R1c and a nucleotide sequence extending from the region R1 having a nucleotide sequence complementary to this nucleotide sequence to the region F1c. X1c and X1 capable of annealing in the inside of the primer can be arbitrary sequences. However, in a region between primers FA and RF, the sequence of the region X1c/X1 is made preferably different.

First, the synthesis of a complementary chain by the primer FA from the region F1 in template nucleic acid is conducted. Then, the region R1c in the synthesized complementary chain is made ready for base pairing, to which the other primer is annealed to form the origin of synthesis of complementary chain. The 3'-terminal of the complementary chain synthesized in this step has a nucleotide sequence complementary to the primer FA constituting the 5'-terminal of the initially synthesized chain, so it has been provided at the 3'-terminal thereof with the region X1 which anneals to the region X1c in the same chain to form a loop. The characteristic 3'-terminal structure according to the present invention is thus provided, and the subsequent reaction constitutes the reaction system shown previously as the most preferable mode. The oligonucleotide annealing to the portion of the loop is provided at the 3'-terminal thereof with the region X2 complementary to the region X2c located in the loop and at the 5'-terminal thereof with the region X1. In the previous reaction system, primers FA and RA were used to synthesize a chain complementary to template nucleic acid thereby giving a loop structure to the 3'-terminal of the nucleic acid. In this method, the terminal structure characteristic of the present invention is provided by the short primers. In this mode, on the other hand, the whole of a nucleotide sequence constituting a loop is provided as a primer, and synthesis of this longer primer is necessary.

If a nucleotide sequence containing restriction enzyme recognition regions is used as a reverse primer, a different mode according to the present invention can be constituted. The reaction with a reverse primer containing a restriction enzyme recognition sequence is specifically described by reference to FIG. 6. When FIG. 6-(D) is completed, a nick is generated by a restriction enzyme corresponding to a restriction enzyme recognition site in the reverse primer. The strand displacement-type reaction of synthesizing complementary chain is initiated from this nick as the origin of synthesis. Because the reverse primers are located at both the terminals of a double-stranded nucleic acid constituting (D), the reaction of synthesizing complementary chain is also initiated from both the terminals. Though basically based on the SDA method described as the prior art, the nucleotide sequence serving as a template has a structure having complementary nucleotide sequences alternately linked according to the present invention so that the nucleic acid synthetic system unique to the present invention is constituted. A part serving as a complementary chain of the reverse primer to be nicked should be designed to incorporate a dNTP derivative such that it is rendered nuclease resistance to prevent cleavage of the double-stranded chain by the restriction enzyme.

It is also possible to insert a promoter for RNA polymerase into the reverse primer. Transcription from both the terminals in FIG. 6-(D) is performed by a RNA polymerase recognizing this promoter in this case too similar to the previous mode where the SDA method was applied.

The nucleic acid synthesized in the present invention is a single-stranded chain but is composed of partial complementary sequences, and thus the majority of these sequences are base-paired. By use of this feature, the synthesized product can be detected. By carrying out the method of synthesizing nucleic acid according to the present invention in the presence of a fluorescent pigment as a double-stranded chain-specific intercalator such as ethidium bromide, SYBR Green I or Pico Green, the increased density of fluorescence is observed as the product is increased. By monitoring it, it is possible to trace the real-time synthetic reaction in a closed system. Application of this type of detection system to the PCR method is also considered, but it is deemed that there are many problems because the signal from the product cannot be distinguished from signals from primer dimers etc. However, when this system is applied to this invention, the possibility of increasing unspecific base pairing is very low, and thus high sensitivity and low noises can be simultaneously expected. Similar to use of the double-stranded chain-specific intercalator, the transfer of fluorescent energy can be utilized for a method of realizing a detection system in a uniform system.

The method of synthesizing nucleic acid according to the present invention is supported by the DNA polymerase catalyzing the strand displacement-type reaction for synthesis of complementary chain. During the reaction described above, a reaction step not necessarily requiring the strand displacement-type polymerase is also contained. However, for simplification of a constitutional reagent and in an economical viewpoint, it is advantageous to use one kind of DNA polymerase. As this kind of DNA polymerase, the following enzymes are known. Further, various mutants of these enzymes can be utilized in the present invention insofar as they have both the sequence-dependent activity for synthesis of complementary chain and the strand displacement activity. The mutants referred to herein include those having only a structure bringing about the catalytic activity required of the enzyme or those with modifications to catalytic activity, stability or thermostability by e.g. mutations in amino acids.

Bst DNA polymerase
Bca (exo-)DNA polymerase
DNA polymerase I Klenow fragment
Vent DNA polymerase
Vent (exo-)DNA polymerase (Vent DNA polymerase deficient in exonuclease activity)
Deep Vent DNA polymerase
Deep Vent(exo-)DNA polymerase (Deep Vent DNA polymerase deficient in exonuclease activity)
Φ29 phage DNA polymerase
MS-2 phage DNA polymerase
Z-Taq DNA polymerase (Takara Shuzo Co., Ltd.)
KOD DNA polymerase (Toyobo Co., Ltd.)

Among these enzymes, Bst DNA polymerase and Bca (exo-) DNA polymerase are particularly desired enzymes because they have a certain degree of thermostability and high catalytic activity. The reaction of this invention can be carried isothermally in a preferred embodiment, but because of the adjustment of melting temperature (Tm) etc., it is not always possible to utilize temperature conditions desired for the stability of the enzyme. Accordingly, it is one of the desired conditions that the enzyme is thermostable. Although the isothermal reaction is feasible, heat denaturation may be conducted to provide nucleic acid as a first template, and in this respect too, utilization of a thermostable enzyme broadens selection of assay protocol.

Vent (exo-) DNA polymerase is an enzyme having both strand displacement activity and a high degree of thermostability. It is known that the complementary chain synthetic reaction involving strand displacement by DNA polymerase is promoted by adding, a single strand binding protein (Paul M. Lizardi et al., Nature Genetics, 19, 225-232, July, 1998). This action is applied to the present invention, and by adding the single strand binding protein, the effect of promoting the synthesis of complementary chain can be expected. For example, T4 gene 32 is effective as a single strand binding protein for Vent (exo-) DNA polymerase.

For DNA polymerase free of 3'-5' exonuclease activity, there is a known phenomenon where the synthesis of complementary chain does not stop at the 5'-terminal of a template, resulting in generation of a one-base protrusion. In the present invention, this phenomenon is not preferable because when synthesis of the complementary chain reaches the terminal, the sequence of the 3'-terminal leads to initiation of next synthesis of complementary chain. However, because a base "A" is added at high probability to the 3'-terminal by the DNA polymerase, the sequence may be selected such that the synthesis from the 3'-terminal starts at "A" so that there is no problem if an additional base is added erroneously by dATP. Further, even if the 3'-terminal is protruded during synthesis of complementary chain, the 3'→5' exonuclease activity can be utilized for digesting the protrusion to make it blunt-ended. For example, since natural vent DNA polymerase has this activity, this enzyme may be used as a mixture with Vent (exo-) DNA polymerase in order to solve this problem.

Various reagents necessary for the method of synthesizing or amplifying nucleic acid according to the present invention may be previously packaged and provided as a kit. Specifically, a kit is provided for the present invention, comprising various kinds of oligonucleotides necessary as primers for synthesis of complementary chain and as outer primers for displacement, dNTP as a substrate for synthesis of complementary chain, a DNA polymerase for carrying out the strand displacement-type synthesis of complementary chain, a buffer giving suitable conditions to the enzyme reaction, and as necessary regents necessary for detection of synthetic reaction products. In particular, the addition of reagents is necessary during the reaction in a preferable mode of the present invention, and thus the reagents necessary for one reaction are supplied after pipetted into reaction vessel, whereby the reaction can be initiated by adding only a sample. By constituting a system in which the reaction product can be detected in situ in a reaction vessel by utilizing a luminescent signal or a fluorescent signal, it is not necessary to open and shut the vessel after reaction. This is very desirable for prevention of contamination.

The nucleic acid having complementary nucleotide sequences alternately linked in a single-stranded chain, synthesized according to the present invention, has e.g. the following usefulness. The first feature is use of an advantage resulting from the special structure having complementary sequences in one molecule. This feature can be expected to facilitate detection. That is, there is a known system for detecting nucleic acid wherein its signal is varied depending on base pairing with a complementary nucleotide sequence. For example, by combination with the method of utilizing a double-stranded chain-specific intercalator as a detector as described above, a detection system making full use of the characteristics of the synthetic product of the present invention can be realized. If the synthetic reaction product of the present invention is once heat-denatured in said detection system and returned to the original temperature, intramolecular annealing occurs preferentially thus permitting complementary sequences to be rapidly base-paired. If there are unspecific reaction products, they have not complementary sequences in the molecule so that after separated by heat denaturation into 2 or more molecules, they cannot immediately be returned to the original double-stranded chain. By providing the step of heat denaturation before detection, noises accompanying the unspecific reaction can be reduced. If the DNA polymerase not resistant to heat is used, the step of heat denaturation has the meaning of termination of the reaction and is thus advantageous for the control of reaction temperature.

The second feature is to always form a loop capable of base pairing. The structure of a loop capable of base pairing is shown in FIG. 4. As can be seen from FIG. 4, the loop is composed of the nucleotide sequence F2c (X2c) which can be annealed by the primer and a nucleotide sequence intervening between F2c-F1c (X1c). The sequence between F2c-F1c (or between X2c-X1c in a more universal form) is a nucleotide derived sequence derived from the template. Accordingly, if a probe having a complementary nucleotide sequence is hybridized with this region, template-specific detection is feasible. In addition, this region is always ready for base pairing, and therefore, heat denaturation prior to hybridization is not necessary. The nucleotide sequence constituting a loop in the amplification reaction product in the present invention may have an arbitrary length. Accordingly, if hybridization with a probe is desired, a region to be annealed by the primer and a region to be hybridized by the probe are arranged separately to prevent their competition, whereby ideal reaction conditions can be constituted.

According to a preferable mode of the present invention, a large number of loops capable of base pairing are given in a single strand of nucleic acid. This means that a large number of probes can be hybridized with one molecule of nucleic acid to permit highly sensitive detection. It is thus possible to realize not only the improvement of sensitivity but also a method of detecting nucleic acid based on a special reaction principle such as aggregation. For example, a probe immobilized onto fine particles such as polystyrene latex is added to the reaction product of the present invention, the aggregation of latex particles is observed as the hybridization of the product with the probe proceeds. Highly sensitive and quantitative observation is feasible by optically measuring the strength of the aggregation. Because the aggregation can also be observed with the naked eyes, a reaction system not using an optical measuring device can also be constituted.

Further, the reaction product of the present invention permitting many labels to be bound thereto per nucleic acid molecule enables chromatographic detection. In the field of immunoassay, an analytical method (immunochromatography) using a chromatographic medium utilizing a visually detectable label is used practically. This method is based on the principle that an analyte is sandwiched between an antibody immobilized on a chromatographic medium and a labeled antibody, and the unreacted labeled component is washed away. The reaction product of the present invention makes this principle applicable to analysis of nucleic acid. That is, a labeled probe toward the part of a loop is prepared and immobilized onto a chromatographic medium to prepare a capturing probe for trapping thereby permitting analysis in the chromatographic medium. As the capturing probe, a sequence complementary to the part of the loop can be utilized. Since the reaction product of the present invention has a large number of loops, the product binds to a large number of labeled probes to give a visually recognizable signal.

The reaction product according to the present invention always giving a region as a loop capable of base pairing enables a wide variety of other detection systems. For example, a detection system utilizing surface plasmon resonance using an immobilized probe for this loop portion is feasible. Further, if a probe for the loop portion is labeled with a double-stranded chain-specific intercalator, more sensitive fluorescent analysis can be conducted. Alternatively, it is also possible to positively utilize the ability of the nucleic acid synthesized by the present invention to form a loop capable of base pairing at both the 3'- and 5'-sides. For example, one loop is designed to have a common nucleotide sequence between a normal type and an abnormal type, while the other loop is designed to generate a difference therebetween. It is possible to constitute a characteristic analytic system in which the presence of a gene is confirmed by the probe for the common portion while the presence of an abnormality is confirmed in the other region. Because the reaction of synthesizing nucleic acid according to the present invention can also proceed isothermally, it is a very important advantage that real-time analysis can be effected by a general fluorescent photometer. Heretofore, the structure of nucleic acid to be annealed in the same chain is known. However, the nucleic acid having complementary nucleotide sequences linked alternately in a single-stranded chain obtained by the present invention is novel in that it contains a large number of loops capable of base pairing with other oligonucleotides.

On the other hand, a large number of loops themselves given by the reaction product according to the present invention can be used as probes. For example, in a DNA chip, probes should be accumulated at high density in a limited area. In present technology, however, the number of oligonucleotides which can be immobilized in a certain area is limited. Hence, by use of the reaction product of the present invention, a large number of probes capable of annealing can be immobilized at high density. That is, the reaction product according to the present invention may be immobilized as probes on a DNA chip. After amplification, the reaction product may be immobilized by any techniques known in the art, or the immobilized oligonucleotide is utilized as the oligonucleotide in the amplification reaction of the present invention, resulting in generating the immobilized reaction product. By use of the probe thus immobilized, a large number of sample DNAs can be hybridized in a limited area, and as a result, high signals can be expected.

BRIEF DESCRIPTION OF THE DRAWINGS

FIG. 7 is a drawing showing the positional relationship of each nucleotide sequence constituting an oligonucleotide in the target nucleotide sequence of M13mp18.

FIG. 11 is a drawing showing the positional relationship of each nucleotide sequence constituting an oligonucleotide in a target nucleotide sequence derived from HVB.

FIG. 14 is a photograph showing the result of agarose gel electrophoresis of a product obtained by the method of synthesizing single-stranded nucleic acid according to the present invention wherein the concentration of M13mp18 as a target was varied. The upper and lower photographs show the result of the reaction for 1 and 3 hours respectively.
Lane 1: M13mp18 dsDNA $1 \times 10^{-15}$ mol/tube
Lane 2: M13mp18 dsDNA $1 \times 10^{-16}$ mol/tube
Lane 3: M13mp18 dsDNA $1 \times 10^{-17}$ mol/tube
Lane 4: M13mp18 dsDNA $1 \times 10^{-18}$ mol/tube
Lane 5: M13mp18 dsDNA $1 \times 10^{-19}$ mol/tube
Lane 6: M13mp18 dsDNA $1 \times 10^{-20}$ mol/tube
Lane 7: M13mp18 dsDNA $1 \times 10^{-21}$ mol/tube
Lane 8: M13mp18 dsDNA $1 \times 10^{-22}$ mol/tube
Lane 9: No target
Lane 10: XIV size marker FIG. 15 is a drawing showing the position of a mutation and the positional relationship of each region toward a target nucleotide sequence (target). Underlined guanine is replaced by adenine in the mutant.

FIG. 17 is a drawing showing the positional relationship of each nucleotide sequence constituting an oligonucleotide in a nucleotide sequence coding for target mRNA.

BEST MODE FOR CARRYING OUT THE INVENTION

Example 1. Amplification of a Region in M13mp18

The method of synthesizing the nucleic acid having complementary chains alternately linked in a single-stranded chain according to the present invention was attempted using M13mp18 as a template. Four kinds of primers, that is, M13FA, M13RA, M13F3, and M13R3, were used in the experiment. M13F3 and M13R3 were outer primers for displacing the first nucleic acid obtained respectively with M13FA and M13RA as the origin of synthesis. Because the outer primers are primers serving as the origin of synthesis of complementary chain after synthesis with M13FA (or M13RA), these were designed to anneal to a region contiguous to M13FA (or M13RA) by use of the phenomenon of contiguous stacking. Further, the concentrations of these primers were set high such that annealing of M13FA (or M13RA) occurred preferentially.

The nucleotide sequence constituting each primer is as shown in the Sequence Listing. The structural characteristics of the primers are summarized below. Further, the positional relationship of each region toward the target nucleotide sequence (target) is shown in FIG. 7.

| Primer | Region at the 5'-side/region at the 3'-side |
|---|---|
| M13FA | The same as region F1c in complementary chain synthesized by M13FA/complementary to region F2c in M13mp18 |
| M13RA | The same as region R1c in complementary chain synthesized by M13RA/complementary to region R2c in complementary chain synthesized by M13FA |
| M13F3 | Complementary to F3c contiguous to the 3'-side of region F2c in M13mp18 |
| M13R3 | Complementary to R3c contiguous to the 3'-side of region F2c in complementary chain synthesized by M13FA |

By such primers, nucleic acid wherein a region extending from F1c to R1c in M13mp18, and its complementary nucleotide sequence, are alternately linked via a loop-forming sequence containing F2c in a single-stranded chain, is synthesized. The composition of a reaction solution for the method of synthesizing nucleic acid by these primers according to the present invention is shown below.
Composition of the reaction solution (in 25 μL)
20 mM Tris-HCl pH8.8
10 mM KCl
10 mM $(NH_4)_2SO_4$
6 mM $MgSO_4$
0.1% Triton X-100
5% dimethyl sulfoxide (DMSO)
0.4 mM dNTP
Primers:
  800 nM M13FA/SEQ ID NO:1
  800 nM M13RA/SEQ ID NO:2
  200 nM M13F3/SEQ ID NO:3
  200 nM M13R3/SEQ ID NO:4
Target: M13mp18 dsDNA/SEQ ID NO:5
Reaction: The above reaction solution was heated at 95° C. for 5 minutes, and the target was denatured into a single-stranded chain. The reaction solution was transferred to ice-cold water, and 4 U of Bst DNA polymerase (NEW ENGLAND Biolabs) was added thereto and the mixture was reacted at 65° C. for 1 hour. After reaction, the reaction was terminated at 80° C. for 10 minutes and transferred again to ice-cold water.

Figure 8:
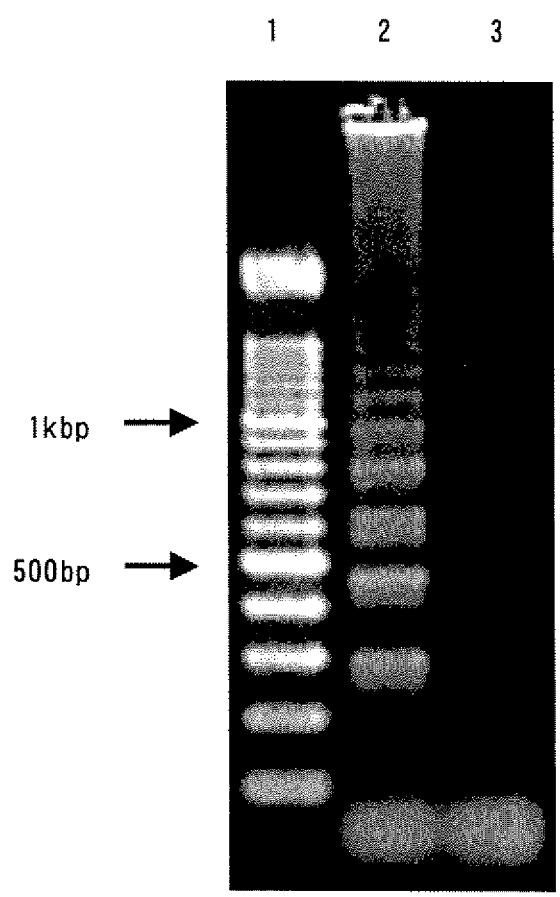
FIG. 8 is a photograph showing the result of agarose electrophoresis of a product obtained by the method of synthesizing single-stranded nucleic acid with M13mp18 as a template according to the present invention.
Lane 1: XIV size marker
Lane 2: 1 fmol M13mp18 dsDNA
Lane 3: No target

Confirmation of the reaction: 1 μl loading buffer was added to 5 μl of the above reaction solution, and the sample was electrophoresed for 1 hour at 80 mV on 2% agarose gel (0.5% TBE). As a molecular-weight marker, XIV (100 bp ladder, Boehringer Mannheim) was used. The gel after electrophoresis was stained with SYBR Green I (Molecular Probes, Inc.) to confirm the nucleic acid. The results are shown in FIG. 8. The respective lanes correspond to the following samples.
1. XIV size marker.
2. 1 fmol M13mp18 dsDNA.
3. No target.

Figure 1:
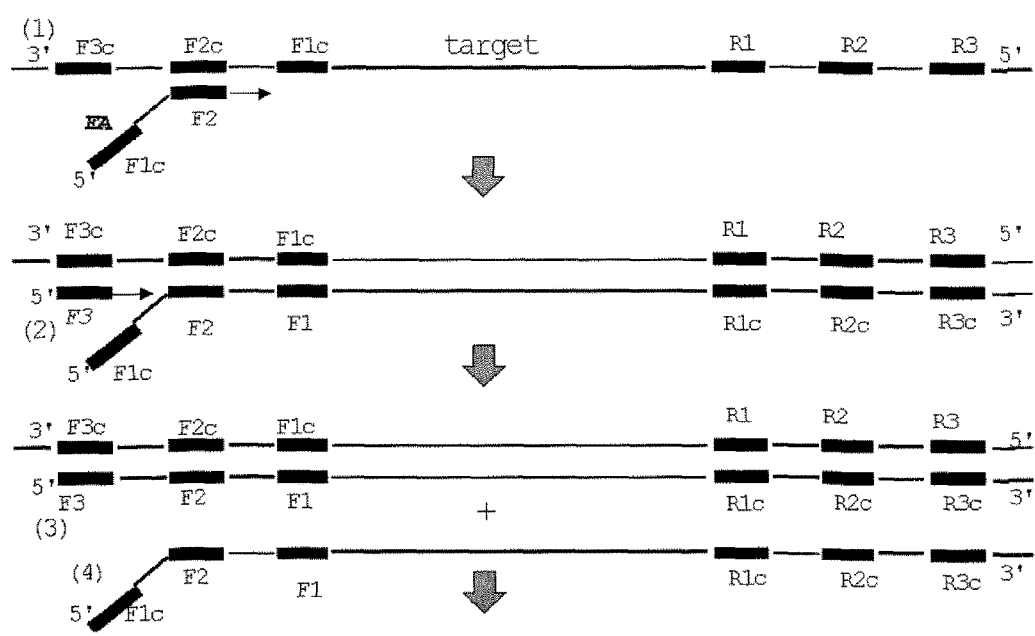
FIG. 1 is an illustration of a part (1) to (4) of the reaction principle in a preferable mode of the present invention.
Figure 2:
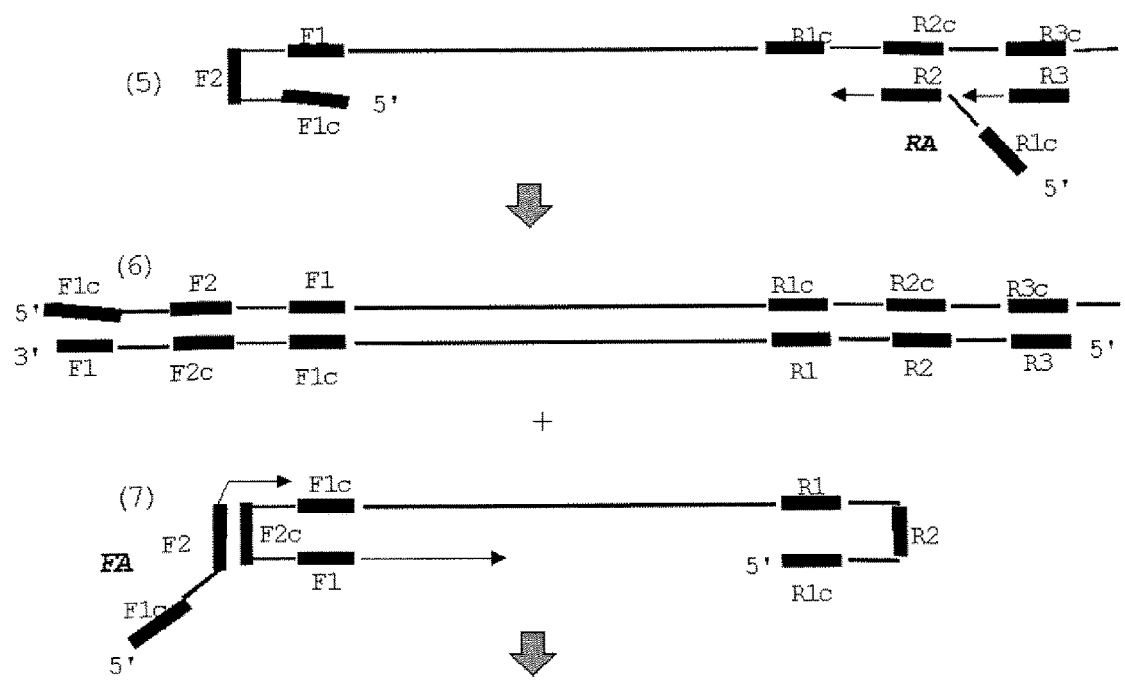
FIG. 2 is an illustration of a part (5) to (7) of the reaction principle in a preferable mode of the present invention.
Figure 3:
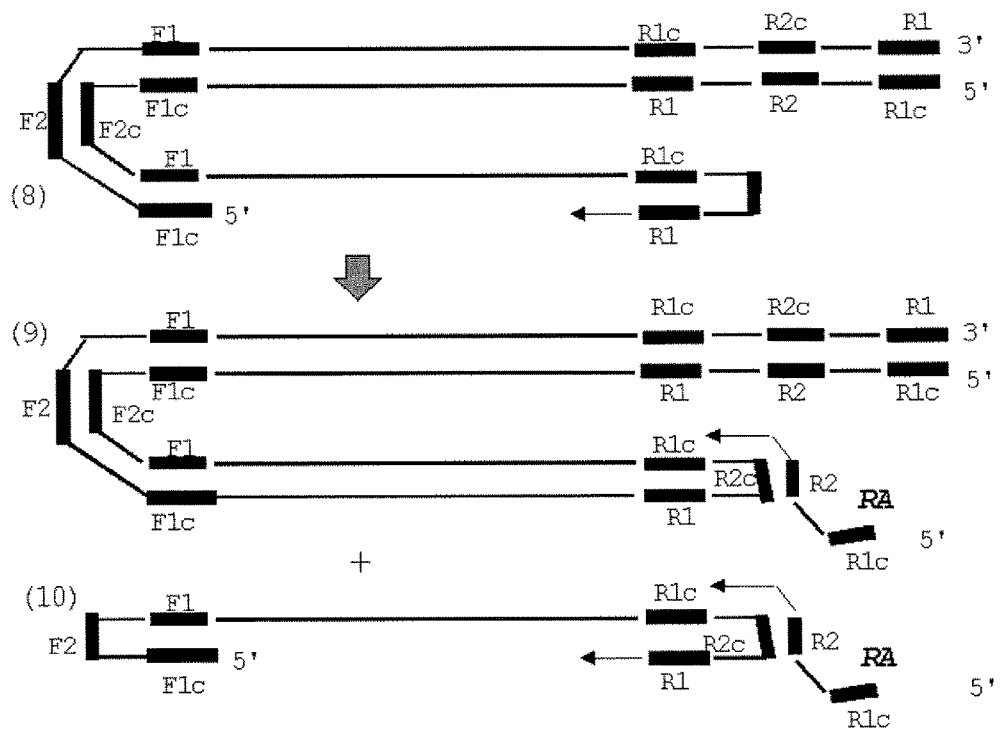
FIG. 3 is an illustration of a part (8) to (10) of the reaction principle in a preferable mode of the present invention.
Figure 4:
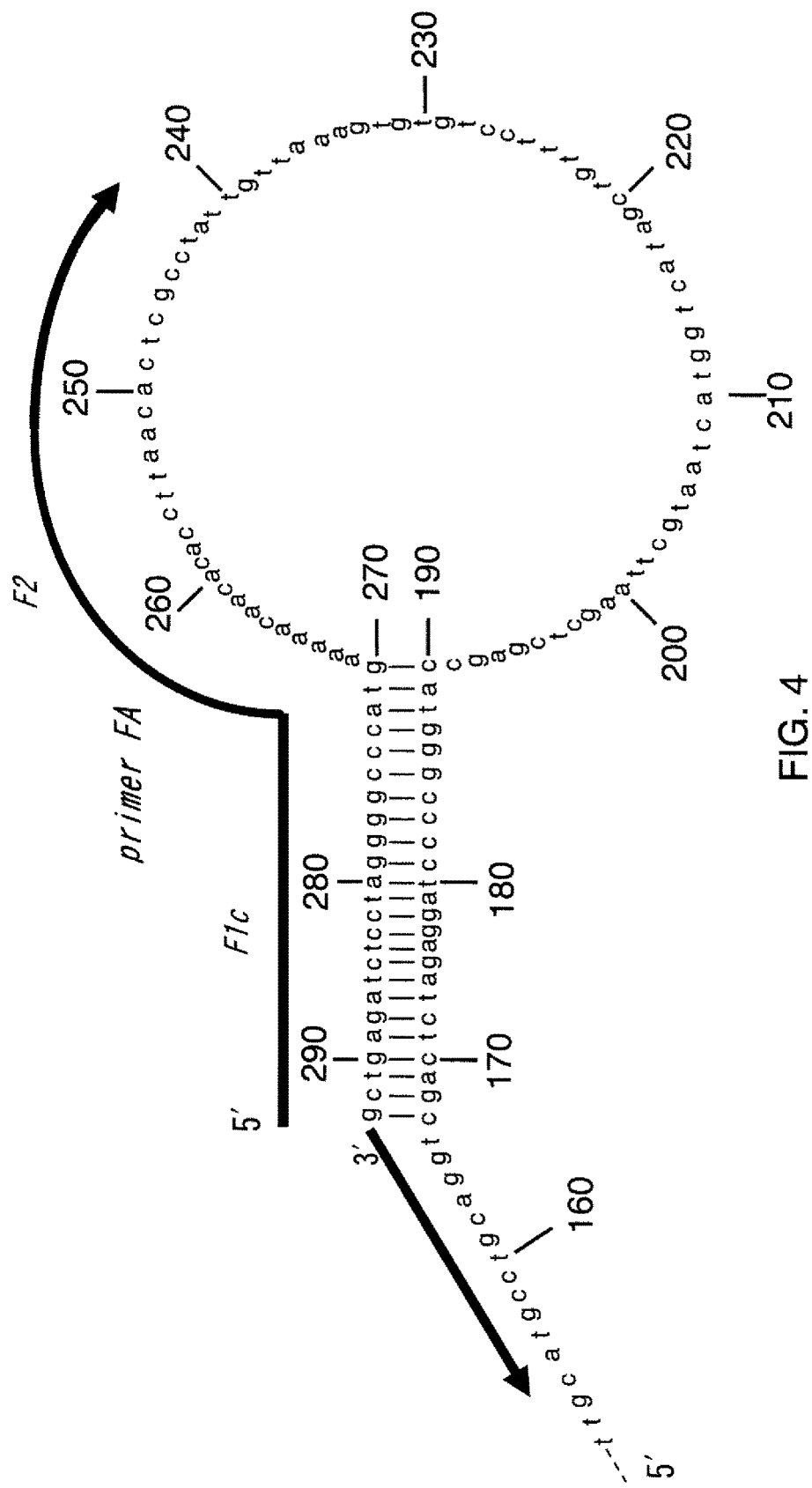
FIG. 4 is an illustration of the structure of a loop formed by the single-stranded nucleic acid according to the present invention.
Figure 5:
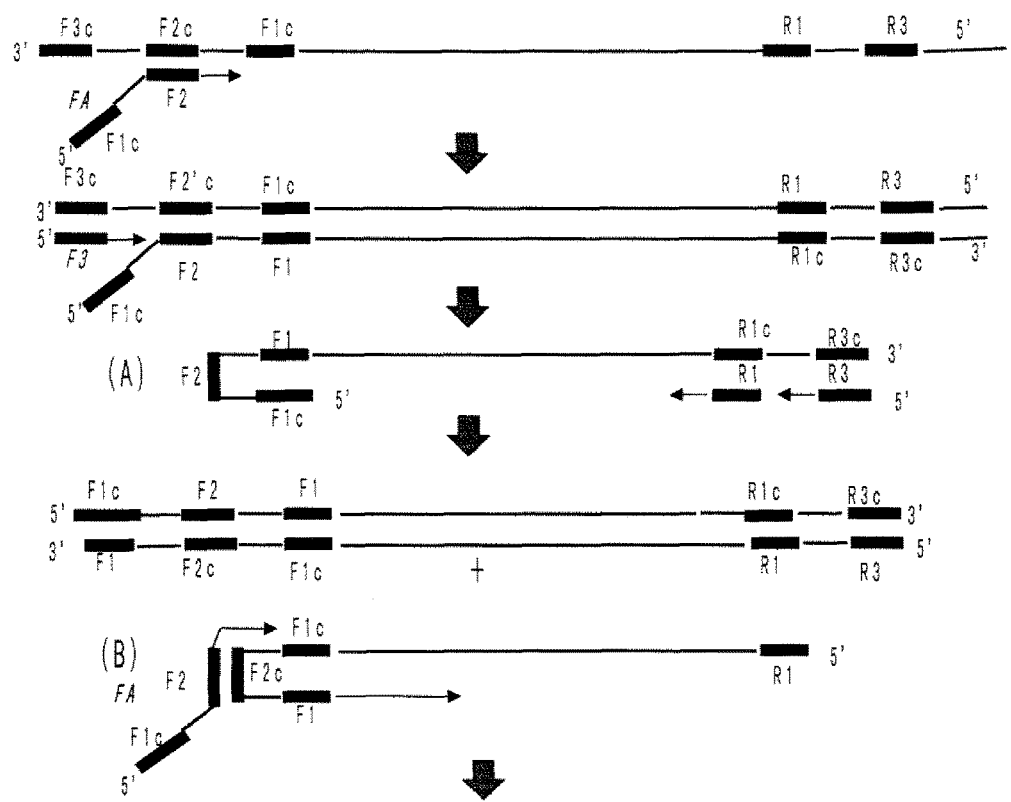
FIG. 5 is an illustration of a part (A) to (B) in a basic mode of the present invention.
Figure 6:
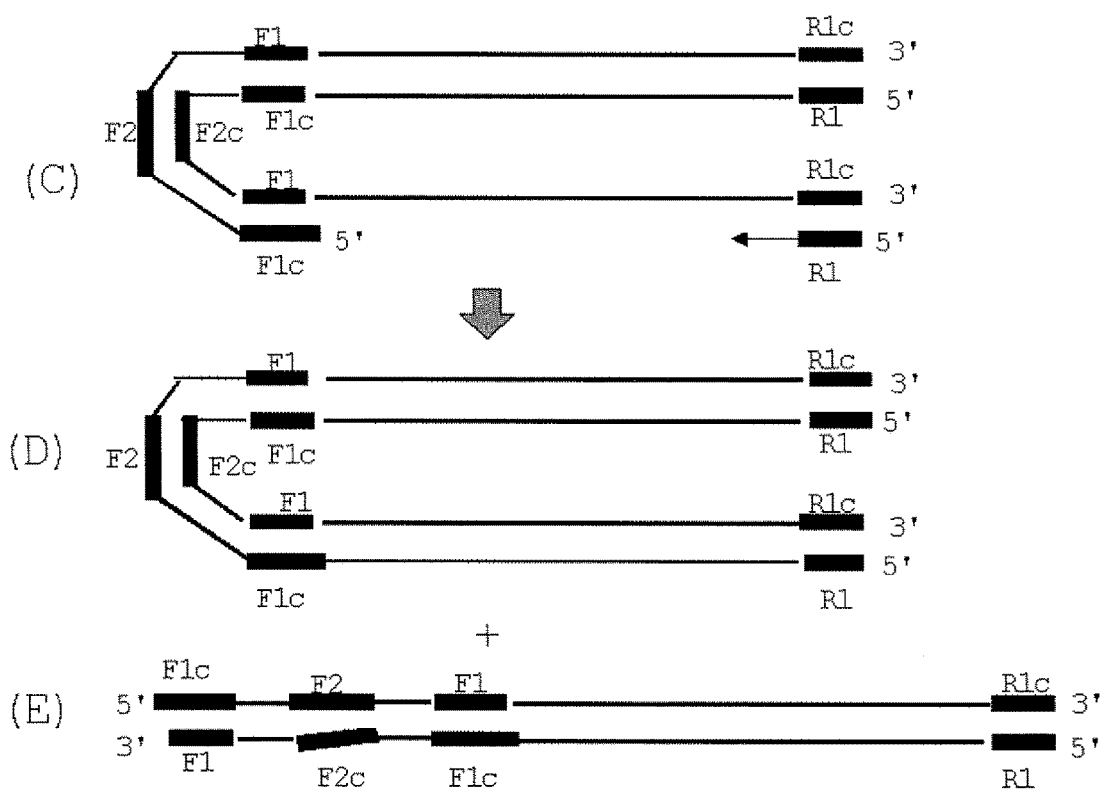
FIG. 6 is an illustration of a part (C) to (D) in a basic mode of the present invention.

In lane 3, no band was confirmed except that the unreacted primers were stained. In lane 2 in the presence of the target, the products were confirmed as a low size band ladder, as smeared staining at high size and as a band hardly electrophoresed in the gel. Among the low-size bands, bands in the vicinity of 290 bp and 450 bp agree with the products estimated in the synthetic reaction of this invention, that is, double-stranded chains of SEQ ID NOS: 11 and 12 (corresponding to double-stranded chains formed as shown in FIGS. 2-(7) and 2-(10)) and a single-stranded chain of SEQ ID NO: 13 (corresponding to the long single-stranded chain in FIG. 3-(9)), and it was thus confirmed that the reaction proceeds as expected. It was estimated that the electrophoresis results of the smeared pattern at high size and the band not electrophoresed were brought about because this reaction was basically a continuous reaction to permit varying molecular weights of the reaction product and further because the product has a complicated structure having a partially single-stranded chain and a double-stranded complex.

Example 2. Confirmation of the Reaction Products by Digestion with Restriction Enzymes For the purpose of clarifying the structure of the nucleic acid having complementary nucleotide sequences linked alternately in a single-stranded chain obtained in Example 1 according to the present invention, the digestion of the products with restriction enzymes was conducted. If fragments are theoretically generated by digestion thereof with restriction enzymes and simultaneously the smear pattern at high size and the band not electrophoresed as observed in Example 1 disappear, then it can be estimated that any of these products are the nucleic acid having complementary sequences linked alternately in a single-stranded chain synthesized according to the present invention.

Figure 9:
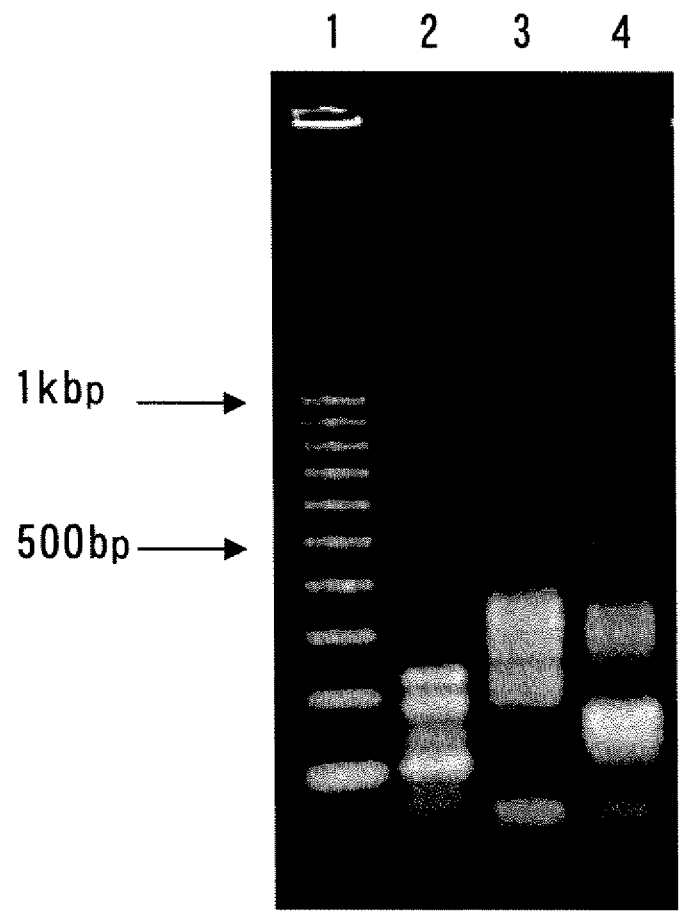
FIG. 9 is a photograph showing the result of agarose gel electrophoresis of a restriction enzyme-digested product obtained in Example 1 by the nucleic acid synthetic reaction according to the present invention.
Lane 1: XIV size marker
Lane 2: BamHI digest of the purified product
Lane 3: PvuII digest of the purified product
Lane 4: HindIII digest of the purified product

The reaction solution (200 μl) from 8 tubes in Example 1 was pooled and purified by treatment with phenol and precipitation with ethanol. The resulting precipitates were recovered and dissolved again in 200 μl TE buffer, and 10 μl aliquot was digested at 37° C. for 2 hours with restriction enzymes BamHI, PvuII, and HindIII respectively. The digest was electrophoresed for 1 hour at 80 mV on 2% agarose gel (0.5% TBE). As a molecular marker, Super Ladder-Low (100 bp ladder) (Gensura Laboratories, Inc.) was used. The gel after electrophoresis was stained with SYBR Green I (Molecular Probes, Inc.) to confirm the nucleic acid. The results are shown in FIG. 9. The respective lanes correspond to the following samples.
1. XIV size marker
2. BamHI digest of the purified product
3. PvuII digest of the purified product
4. HindIII digest of the purified product It is estimated that nucleotide sequences constituting relatively short amplification products are those of SEQ ID NOS:13, 14, 15 and 16. From these nucleotide sequences, the estimated size of each fragment digested with the restriction enzymes is as shown in Table 1. "L" in the table indicates that its position in electrophoresis is not established because L is a fragment containing a loop (single-stranded chain).

TABLE 1

Restriction enzyme-digested fragments of the amplification products according to the present invention

| SEQ ID NO | BamHI | PvuII | HindIII |
|---|---|---|---|
| 13 | 177 + L | 56 + L | 147 + L |
| 14 | 15 + 101 + L | — | 142 + L |
| 15 | 171 + 101 + L | 56 + L | 147 + 161 + L |
| 16 | 11 + 101 + 230 + L | 237 + L | 142 + 170 + L |
| Summary | 101, 177, 230 | 56, 237 | 142, 147, 161, 170 |

(11, 15; not confirmed)

Because almost all bands before digestion were changed into estimated bands, it was confirmed that the object reaction products were amplified. Further, it was also shown that there were no or less unspecific products.

Example 3. Promotion of Amplification Reaction by Addition of Betaine

An experiment for examining the effect of betaine (N,N,N-trimethylglycine, Sigma) added to the amplification reaction solution on the amplification reaction of nucleic acid was conducted. Synthesis of the nucleic acid having complementary chains alternately linked in a single-stranded chain according to the present invention was conducted using M13mp18 as a template similarly in Example 1 in the presence of betaine at various concentrations. The primers used in the experiment were identical to those used in Example 1. The amount of the template DNA was $10^{-21}$ mol (M13mp18) and water was used as the negative control. Betaine was added at concentrations of 0, 0.5, 1 and 2 M to the reaction solution. The composition of the reaction solution is shown below.
Composition of the reaction solution (in 25 μL)
20 mM Tris-HCl pH8.8
4 mM MgSO$_4$
0.4 mM dNTPs
10 mM KCl
10 mM (NH$_4$)$_2$SO$_4$
0.1% Triton X-100
Primers:
  800 nM M13FA/SEQ ID NO:1
  800 nM M13RA/SEQ ID NO:2
  200 nM M13F3/SEQ ID NO:3
  200 nM M13R3/SEQ ID NO:4
Target: M13mp18 dsDNA/SEQ ID NO:5

The polymerase, reaction conditions, and conditions for electrophoresis after the reaction were identical to those described in Example 1.

Figure 10:
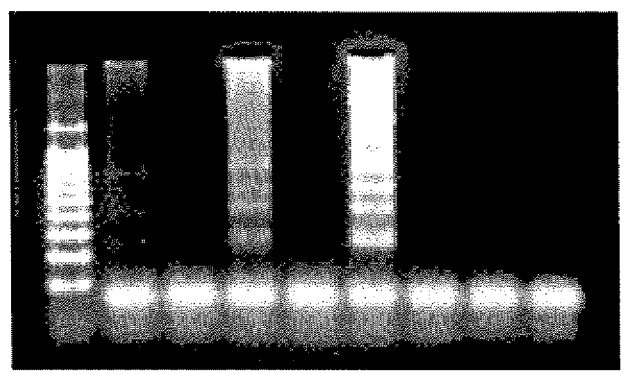
FIG. 10 is a photograph showing the result of agarose gel electrophoresis of a product obtained, by the method of synthesizing single-stranded nucleic acid according to the present invention using M13mp18 as a template in the presence of betaine. 0, 0.5, 1 and 2 indicate the concentration (M) of betaine added to the reaction solution. N indicates the negative control, and −21 indicates the concentration $10^{-21}$ mol of template DNA.

The results are shown in FIG. 10. In the reaction in the presence of betaine at a concentration of 0.5 or 1.0 M, the amount of the amplification product was increased. Further, if its concentration was increased to 2.0 M, no amplification was observed. It was thus shown that the amplification reaction was promoted in the presence of betaine at a suitable concentration. The estimated reason that the amount of the amplification product was decreased when the concentration of betaine was 2 M was that Tm was lowered too much.

Example 4. Amplification of HBV Gene Sequence

The method of synthesizing nucleic acid according to the present invention was attempted wherein M13mp18 dsDNA having a partial sequence of HBV gene integrated therein was used as a template. Four kinds of primers, HB65FA (SEQ ID NO: 6), HB65RA (SEQ ID NO:7), HBF3 (SEQ ID NO:8) and HBR3 (SEQ ID NO:9), were used in the experiment. HBF3 and HBR3 were outer primers for displacement of the first nucleic acid obtained respectively with HB65FA and HB65RA as the origin of synthesis. Because the outer primers are primers serving as the origin of synthesis of complementary chain after synthesis with HB65FA (or HB65RA), these were designed to anneal to a region contiguous to HB65FA (or HB65RA) by use of the phenomenon of contiguous stacking. Further, the concentrations of these primers were set high such that annealing of HB65FA (or HB65RA) occurred preferentially. The target sequence (430 bp) in this example, derived from HBV integrated in M13mp18, is shown in SEQ ID NO:10.

The nucleotide sequence constituting each primer is shown in the Sequence Listing. The structural feature of each primer is summarized below. Further, the positional relationship of each region toward the target nucleotide sequence (target) is shown in FIG. 11.

| Primer | Region at the 5'-side/region at the 3'-side |
|---|---|
| HB65FA | The same as region F1c in complementary chain synthesized by HB65FA/complementary to region F2c in HBV-M13mp18 |
| HB65RA | The same as region R1c in complementary chain synthesized by HB65RA/complementary to region R2c in complementary chain synthesized by HB65FA |
| HBF3 | Complementary to F3c contiguous to the 3'-side of region F2c in HBV-M13mp18 |
| HBR3 | Complementary to R3c contiguous to the 3'-side of region F2c in complementary chain synthesized by HB65FA |

Figure 12:
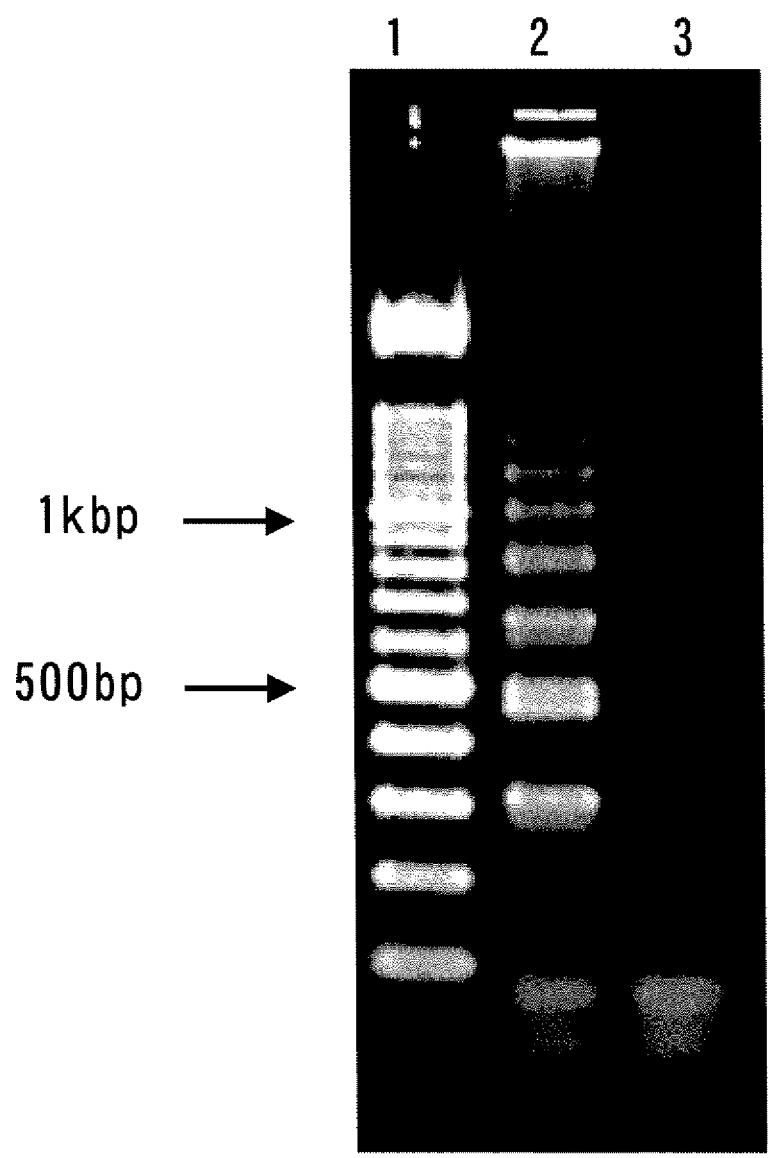
FIG. 12 is a photograph showing the result of agarose gel electrophoresis of a product obtained by the method of synthesizing single-stranded nucleic acid according to the present invention wherein HBV-M13mp18 integrated in M13mp18 was used as a template.
Lane 1: XIV size marker
Lane 2: 1 fmol HBV-M13mp18 dsDNA
Lane 3: No target

By such primers, nucleic acid wherein a region extending from F1c to R1c in M13mp18 (HBV-M13mp18) having a partial sequence of HBV gene integrated therein, and its complementary nucleotide sequence, are alternately linked via a loop-forming sequence containing F2c in a single-stranded chain, is synthesized. The reaction was conducted under the same conditions as in Example 1 except that the primers described above were used, and the reaction solution was analyzed by agarose electrophoresis. The results are shown in FIG. 12. The respective lanes correspond to the following samples.
1. XIV size marker
1 fmol HBV-M13mp18 dsDNA.
3. No target Similar to Example 1, the products were confirmed only in the presence of the target as a low size band ladder, as smeared staining at high size and as a band hardly electrophoresed in the gel (lane 2). Among the low-size bands, bands in the vicinity of 310 bp and 480 bp agree with the products estimated in the synthetic reaction of this invention, that is, double-stranded chains of SEQ ID NOS:17 and 18, and it was thus confirmed that the reaction proceeds as expected. As described in the results in Example 1, it was estimated that the smeared pattern at high size and the band not electrophoresed were caused by the structure of the synthetic product characteristic of the present invention. From this experiment, it was confirmed that the present invention can be practiced even if a different sequence (target) is used for amplification.

Example 5. Confirmation of the Sizes of the Synthetic Reaction Products

Figure 13:
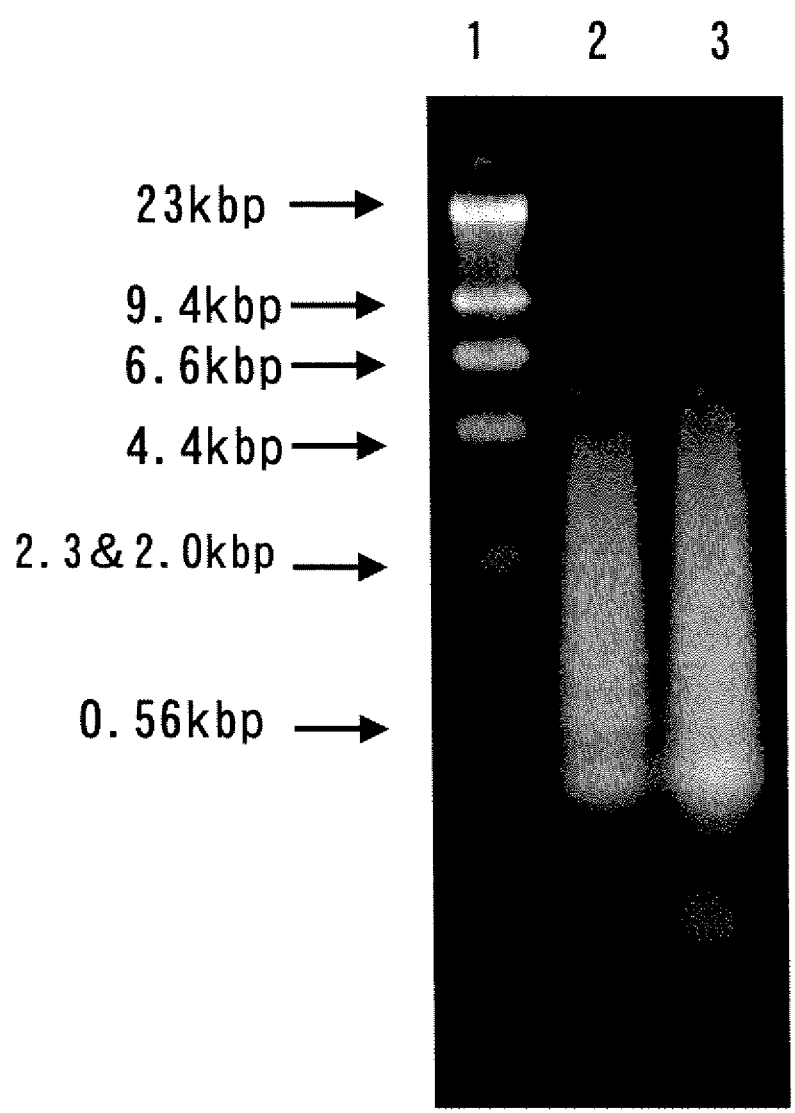
FIG. 13 is a photograph showing the result of gel electrophoresis of an alkali-denatured product obtained by the method of synthesizing single-stranded nucleic acid according to the present invention.
Lane 1: HindIII-digested fragment from lambda-phage
Lane 2: The reaction product in Example 1.
Lane 3: The reaction product in Example 3.

To confirm the structure of the nucleic acid synthesized according to the present invention, its length was analyzed by electrophoresis under alkali-denaturing conditions. 1 μl alkaline loading buffer was added to 5 μl of each reaction solution in the presence of the target in Example 1 or 4 and electrophoresed at 50 mA in 0.7% agarose gel (50 mM NaOH, 1 mM EDTA) for 14 hours. As the molecular-weight size marker, HindIII-digested lambda-phage fragments were used. The gel after electrophoresis was neutralized with 1 M Tris, pH 8 and stained with SYBR Green I (Molecular Probes, Inc.) to confirm the nucleic acid. The results are shown in FIG. 13. The respective lanes correspond to the following samples.
1. HindIII-digested fragments from lambda-phage.
2. The reaction product in Example 1.
3. The reaction product in Example 4.

When the reaction product was electrophoresed under alkali-denaturing conditions, its size in a single-stranded state could be confirmed. It was confirmed that the sizes of the major products in both Example 1 (lane 2) and Example 4 (lane 3) were within 2 kbase. Further, it was revealed that the product according to the present invention had been extended to have a size of at least 6 kbase or more within the range capable of confirmation by this analysis. In addition, it was confirmed again that bands not electrophoresed under non-denaturing conditions in Examples 1 and 4 were separated in a denatured state into individual single-stranded chains of smaller size.

Example 6. Confirmation of Amplification Depending on The Concentration of a Target in the Amplification of a Region in M-13mp13

The influence of a varying concentration of a target on the method of synthesizing nucleic acid according to the present invention was observed. The method of synthesizing nucleic acid according to the present invention was carried out under the same conditions as in Example 1 except that the amount of M13mp18 dsDNA as the target was 0 to 1 fmol and the reaction time was 1 hour or 3 hours. Similar to Example 1, the sample was electrophoresed in 2% agarose gel (0.5% TBE) and stained with SYBR Green I (Molecular Probes, Inc.) to confirm the nucleic acid. As a molecular size marker, XIV (100 bp ladder, Boehringer Mannheim) was used. The results are shown in FIG. 14 (upper: 1-hour reaction, below: 3-hour reaction). The respective lanes correspond to the following samples:
1. M13mp18 dsDNA 1×10−15 mol/tube.
2. M13mp18 dsDNA 1×10−16 mol/tube.
3. M13mp18 dsDNA 1×10−17 mol/tube.
4. M13mp18 dsDNA 1×10−18 mol/tube.
5. M13mp18 dsDNA 1×10−19 mol/tube.
6. M13mp18 dsDNA 1×10−20 mol/tube.
7. M13mp18 dsDNA 1×10−21 mol/tube.
B. M13mp18 dsDNA 1×10−22 mol/tube.
9. No target.
10. XIV size marker.

A common band among the respective lanes appears in a lower part in the electrophoretic profile and shows the unreacted stained primers. Regardless of the reaction time, no amplification product is observed in the absence of the target. A staining pattern, depending on the concentration of the target, of the amplification product was obtained only in the presence of the target. Further, the amplification product could be confirmed at lower concentration as the reaction time was increased.

Example 7. Detection of a Point Mutation (1) Preparation of M13mp18FM (Mutant)

The target DNA used was M13mp18 (wild-type) and M13mp18FM (mutant). For the construction of the mutant M13mp18FM, LA PCR™ in vitro Mutagenesis Kit (Takara Shuzo Co., Ltd.) was used to replace one nucleotide for mutation. Thereafter, the sequence was confirmed by sequencing. The sequence of the F1 region is shown below:

```
wild-type:   CCGGGGATCCTCTAGAGTCG  (SEQ ID NO: 19)

Mutant:      CCGGGGATCCTCTAGAGTCA  (SEQ ID NO: 20)
```

(2) Design of Primers

The FA primers used for the wild-type and the mutant were provided at the 5'-terminal of the F1c region thereof with different nucleotide sequences, respectively. The location of the mutation and the positional relationship of each region toward the target nucleotide sequence (target) are shown in FIG. 15.

(3) Amplification Reaction

An experiment was conducted to examine whether template-specific amplification reaction occurs using a combination of specific primers shown below by use of M13mp18 (wild-type) and M13mp18FM (mutant) as primers.
Primer set for wild-type amplification: FAd4, RAd4, F3, R3
Primer set for mutant amplification: FAMd4, RAd4, F3, R3

The nucleotide sequence of each primer is as follows:

```
FAd4:
                                    (SEQ ID NO: 21)
CAGACTCTAGAGGATCCCCGGTTTTTGTTGTGTGGAATTGTGAGCGGAT

FAMd4:
                                    (SEQ ID NO: 22)
TGACTCTAGAGGATCCCCGGTTTTTGTTGTGTGGAATTGTGAGCGGAT

RAd4:
                                    (SEQ ID NO: 23)
CGTCGTGACTGGGAAAACCCTTTTTGTGCGGGCCTCTTCGCTATTAC

F3:
                                    (SEQ ID NO: 24)
ACTTTATGCTTCCGGCTCGTA

R3:
                                    (SEQ ID NO: 25)
GTTGGGAAGGGCGATCG
```

(4) Detection of the Point Mutation in M13mp18

The composition of the reaction solution is as follows:

|  | Final concentration |  |
|---|---|---|
| D2W | 3.75 µL |  |
| 10x Thermo pol buffer(NEB) | 2.5 µL | 20 mM Tris-HCl pH 8.8 |
|  |  | 10 mM KCl |
|  |  | 10 mM (NH$_4$)$_2$SO$_4$ |
|  |  | 6 mM MgSO$_4$ |
|  |  | 0.1% TritonX-100 |
| 2.5 mM dNTP | 4 µL | 400 µM |
| 100 mM MgSO$_4$ | 0.5 µL |  |
| 4M Betaine | 6.25 µL | 1M |
| M13FAd4 primer (10 pmol/µL) or M13FAMd4 primer (10 pmol/µL) | 2 µL | 800 nM |
| M13RAd4 primer (10 pmol/µL) | 2 µL | 800 nM |
| M13F3 primer (10 pmol/µL) | 0.5 µL | 200 nM |
| M13R3 primer (10 pmol/µL) | 0.5 µL | 200 nM |
| Total amount | 22 µL |  |

1 fmol (2 µl) of the target M13mp18 or M13mp18FM was added to the reaction solution and heated at 95° C. for 5 minutes whereby the target was denatured into a single-stranded chain. The reaction solution was transferred to ice-cold water, and 1 µl (8 U) of Bst DNA polymerase (NEW ENGLAND Biolab) was added thereto and reacted for 1 hour at 68° C. or 68.5° C. After reaction, the reaction was terminated at 80° C. for 10 minutes, and the reaction solution was transferred again to ice-cold water.

Figure 16:
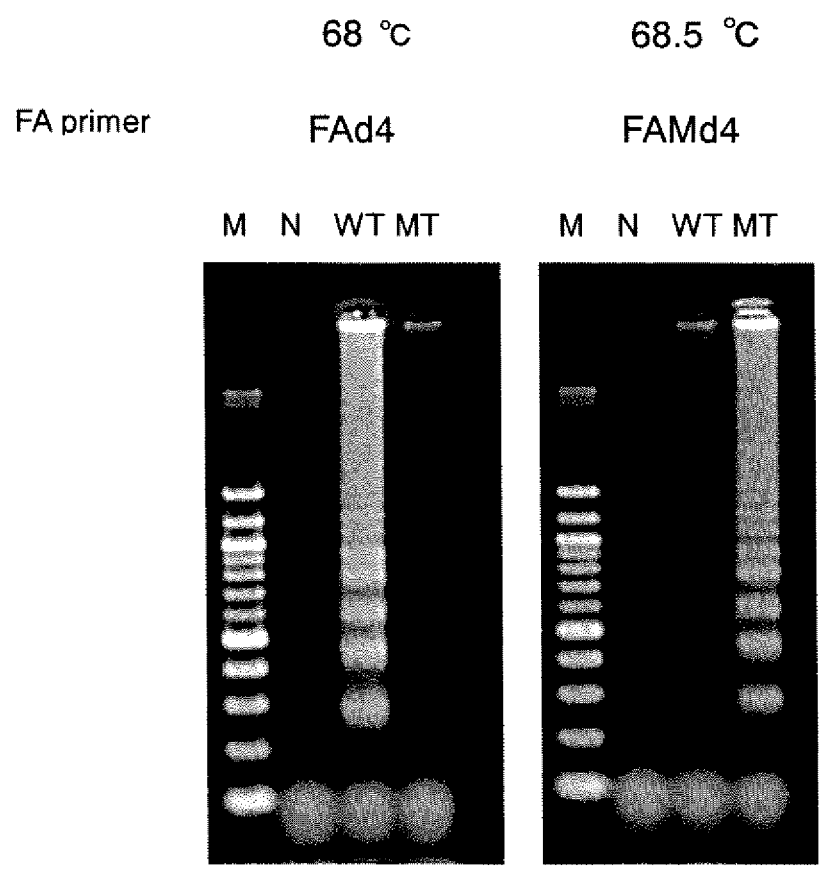
FIG. 16 is a photograph showing the result of agarose gel electrophoresis of a product according to the amplification reaction of the present invention.
M: 100 bp ladder (New England Biolabs)
N: No template (purified water)
WT: 1 fmol wild-type template M13mp18
MT: 1 fmol mutant template M13mp18FM
Figure 18:
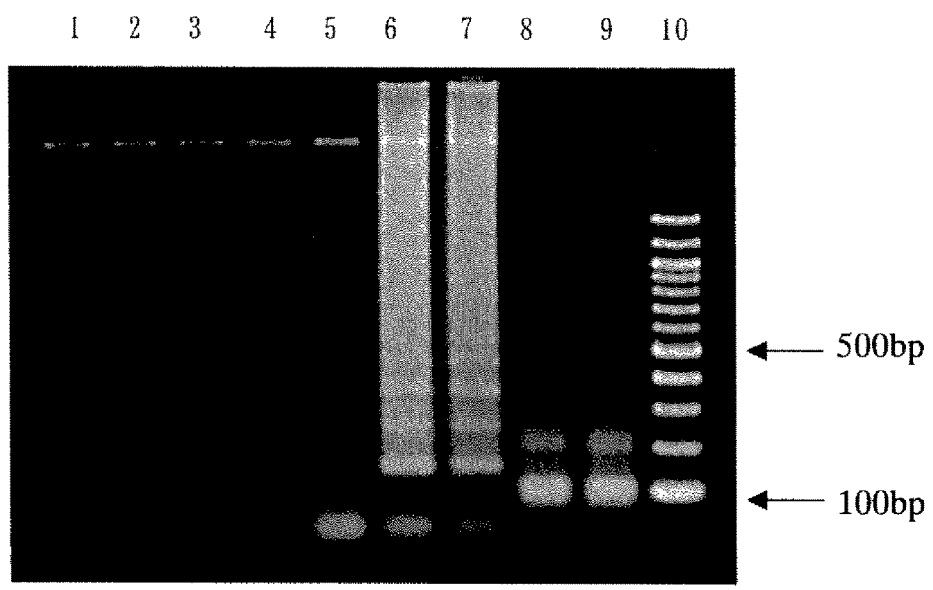
FIG. 18 is a photograph showing the result of agarose electrophoresis of a product obtained by the method of synthesizing single-stranded nucleic acid according to the present invention using mRNA as a target.

As shown in FIG. 16, when FAd4 for wild type was used as the FA primer, effective amplification was observed only in the presence of the wild-type template. On the other hand, when FAMd4 for mutant was used as the FA primer, effective amplification was observed only in the presence of the wild-type [sic.] template.

From the results described above, it was shown that the point mutation could be detected efficiently by use of the amplification reaction of the present invention.

Example 8. Amplification Reaction of mRNA as a Target

The method of synthesizing nucleic acid according to the present invention was attempted using mRNA as the target nucleic acid. To prepare the target mRNA, prostate cancer cell line LNCaP cells (ATCC No. CRL-1740) expressing prostate specific antigen (PSA) were mixed with chronic myeloid leukemia cell line K562 cells (ATCC No. CCL-243) as non-expressing cells at $1:10^6$ to $100:10^6$, followed by extraction of the total RNA by use of an RNeasy Mini kit from Qiagen (Germany). Four kinds of primers, that is, PSAFA, PSARA, PSAF3 and PSAR3, were used in the experiment. PSAF3 and PSAR3 are outer primers for displacing the first nucleic acid obtained respectively with PSAFA and PSARA as the origin of synthesis. Further, the concentrations of these primers were set high such that annealing of PSAFA (or PSARA) occurred preferentially. The nucleotide sequences constituting the respective primers are as follows.

```
Primer:
PSAFA:
                                      (SEQ ID NO: 26)
TGTTCCTGATGCAGTGGGCAGCTTTAGTCTGCGGCGGTGTTCTG PSARA:
                                      (SEQ ID NO: 27)
TGCTGGGTCGGCACAGCCTGAAGCTGACCTGAAATACCTGGCCTG

PSAF3:
                                      (SEQ ID NO: 28)
TGCTTGTGGCCTCTCGTG

PSAR3:
                                      (SEQ ID NO: 29)
GGGTGTGGGAAGCTGTG
```

The structural features of the primers are summarized below. Further, the positional relationship of each primer toward the DNA nucleotide sequence coding for the target mRNA and recognition sites of restriction enzyme Sau3AI are shown in FIG. 17.

| Primer | Region at the 5'-side/region at the 3'-side |
|---|---|
| PSAFA | The same as region F1c in complementary chain synthesized by PSAFA/complementary to region F2c in the target nucleotide sequence |
| PSARA | The same as region R1c in complementary chain synthesized by PSARA/complementary to region R2c in complementary chain synthesized by PSAFA |
| PSAF3 | Complementary to F3c contiguous to the 3'-side of region F2c in the target nucleotide sequence |
| PSAR3 | Complementary to R3c contiguous to the 3'-side of region R2c in complementary chain synthesized by PSAFA |

The composition of a reaction solution for the method of synthesizing nucleic acid according to the present invention is as follows:
Composition of the reaction solution (in 25 µl)
20 mM Tris-HCl pH 8.8
4 mM MgSO$_4$
0.4 mM dNTPs
10 mM KCl
10 mM (NH$_4$)$_2$SO$_4$
0.1% Triton X-100
0.8 M betaine
5 mM DTT
1600 nM PSAFA & PSARA primer
200 nM PSAF3 & PSAR3 primer
8 U Bst DNA polymerase
100 U Rever Tra Ace (Toyobo Co., Ltd., Japan)
5 µg total RNA All ingredients were mixed on ice. In this experiment, mRNA (single-stranded chain) is used as a target, and thus the step of making single-stranded chain by heat denaturation is not necessary. The reaction was conducted at 65° C. for 45 minutes, and the reaction was terminated at 85° C. for 5 minutes. After reaction, 5 µl of the reaction solution was electrophoresed in 2% agarose and detected by SYBR Green I.

The results are shown in Table 18. The respective lanes correspond to the following samples.

| Lane | Bst | RT | Number of LNCaP cells/ $10^6$ K562 cells |
|---|---|---|---|
| 1 | − | + | 0 |
| 2 | − | + | 10 |
| 3 | + | − | 0 |
| 4 | + | − | 10 |
| 5 | + | + | 0 |
| 6 | + | + | 1 |
| 7 | + | + | 10 |
| 8 | | | Sau3AI digest of 1 µL aliquot of the reaction solution in lane 6 |
| 9 | | | Sau3AI digest of 1 µL aliquot of the reaction solution in lane 7 |
| 10 | | | Size maker, 100 bp ladder (New England Biolabs) |

In the absence of either Bst DNA polymerase or Rever Tra Ace, no amplification product could be obtained (lanes 1 to 4). In the presence of both the enzymes, an amplification product was detected (lanes 5 to 7) if RNA derived from LNCaP was present. RNA extracted from one LNCaP cell/one million K562 cells could be detected (lane 6). When the amplification product was digested at the restriction enzyme site Sau3AI located in the inside of the target, the product was digested into a fragment of estimated size (lanes 8 and 9).

From the results described above, it was confirmed that the desired reaction product can be obtained in the method of synthesizing nucleic acid according to the present invention even if RNA is used as a target.

INDUSTRIAL APPLICABILITY

According to the novel oligonucleotide according to the present invention and the method of synthesizing nucleic acid by using said oligonucleotide, there is provided a method of synthesizing nucleic acid having complementary nucleotide sequences linked alternately in a single-stranded chain, without requiring any complicated control of temperature. A complementary chain synthesized with the oligonucleotide as a primer based on the present invention serves as the origin of synthesizing a new complementary chain with the 3'-terminal of said synthesized chain as a template. This is accompanied by formation of a loop causing annealing of a new primer, and a product of the reaction of synthesizing complementary chain with the previously synthesized chain as a template is displaced again by synthesis of complementary chain from the loop and made ready for base pairing. The thus obtained nucleic acid synthesized with itself as a template is combined with e.g. a known nucleic acid synthesizing method such as SDA, to contribute the improvement of efficiency of nucleic acid synthesis.

According to an additional preferred mode of the present invention, there is provided a novel method of synthesizing nucleic acid, which achieves the improvement of efficiency of the known method of synthesizing nucleic acid, does not require complicated control of temperature, can be expected to attain high efficiency of amplification and can achieve high specificity. That is the oligonucleotide based on the present invention is applied to a template chain and its complementary chain whereby nucleic acid having complementary sequences linked alternately in a single-stranded chain can be successively synthesized. This reaction continues theoretically until the starting materials necessary for synthesis are exhausted, during which new nucleic acid initiated to be synthesized from the loop continues to be formed. The elongation from the oligonucleotide having annealed to the loop performs strand displacement for supplying 3'-OH for elongation of long single-stranded nucleic acid (that is, nucleic acid having plural pairs of complementary chains linked therein). On the other hand, the 3'-OH of the long single-stranded chain performs the reaction of synthesizing complementary chain with itself as a template whereby its elongation is achieved, during which a new complementary chain whose synthesis is initiated from the loop is displaced. Such an amplification reaction step proceeds under isothermal conditions while maintaining high specificity.

The oligonucleotides in the present invention can, when two contiguous regions are arranged as designed, function as primers for the reaction of synthesizing nucleic acid according to the present invention. This contributes significantly to the preservation of specificity. By comparison with e.g. PCR where unspecific amplification reaction is initiated by unspecific missannealing regardless of the intended positional relationship of 2 primers, it can be easily explained that high specificity can be expected in the present invention. This feature can be utilized to detect SNPs highly sensitively and accurately.

The characterizing feature of the present invention lies in that such reaction can be easily achieved by a very simple constitution of reagents. For example, the oligonucleotide according to the present invention has a special structure, but this is a matter of selection of nucleotide sequence, and it is a simple oligonucleotide as substance. Further, in a preferred mode, the reaction can proceed by only a DNA polymerase catalyzing the strand displacement-type reaction of synthesizing complementary chain. Further, if the present invention is carried out with RNA as a template, a DNA polymerase such as Bca DNA polymerase having both reverse transcriptase activity and strand displacement-type DNA polymerase activity is used so that all enzyme reactions can be conducted by the single enzyme. The reaction principle of realizing a high degree of nucleic acid amplification reaction by such simple enzyme reaction is not known. Even for the application of the present invention to a known nucleic acid synthesizing reaction such as SDA, no additional enzyme is necessary for their combination, and such a simple combination with the oligonucleotide based on the present invention can be applied to various reaction systems. Accordingly, it can be said that the method of synthesizing nucleic acid according to the present invention is also advantageous in respect of cost.

As described above, the method of synthesizing nucleic acid according to the present invention and the oligonucleotide therefor provide a new principle of simultaneously solving a plurality of difficult problems such as operativeness (temperature control is not necessary), improvement of efficiency of synthesis, economization, and high specificity.

The invention claimed is:

1. A kit designed for synthesizing nucleic acid by amplifying a template nucleic acid comprising a region F3c, a region F2c and a region F1c in this order from the 3'-side of the template, a region R3 and a region R2 in this order from the 5'-side of the template, and a region R1 linked to the 3'-side of the region R2, the kit comprising:
   a first oligonucleotide having 20 to 200 base pairs and comprising a region F2 having a nucleotide sequence complementary to the region F2c and another region F1c linked to the 5'-side of the region F2 and having the same nucleotide sequence as the region F1c;
   a second oligonucleotide having 20 to 200 base pairs and comprising another region R2 having the same nucleotide sequence as the region R2 and a region R1c having a nucleotide sequence complementary to the region R1 and linked to the 5'-side of the another R2 region;
   a third oligonucleotide having 10 to 200 base pairs and comprising a region F3 having a nucleotide sequence complementary to the region F3c; and
   a fourth oligonucleotide having 10 to 200 base pairs and comprising another region R3;
   a DNA polymerase catalyzing a strand displacement-type reaction; and
   a nucleotide serving as a substrate for the DNA polymerase;
   wherein said kit does not include a restriction enzyme and wherein each of the regions is at least 10 bases long.

2. The kit according to claim 1, further comprising a detector for detection of a product of nucleic acid synthetic reaction.

3. A primer set designed for synthesizing nucleic acid by amplifying a template nucleic acid comprising a region F3c, a region F2c and a region F1c in this order from the 3'-side of the template, a region R3 and a region R2 in this order from the 5'-side of the template and a region R1 linked to the 3'-side of the region R2, the set comprising:
   a first oligonucleotide having 20 to 200 base pairs and comprising a region F2 having a nucleotide sequence complementary to the region F2c and another region F1c linked to the 5'-side of the region F2 and having the same nucleotide sequence as the region F1c;
   a second oligonucleotide having 20 to 200 base pairs and comprising another region R2 having the same nucleotide sequence as the region R2 and a region R1c having a nucleotide sequence complementary to the region R1 and linked to the 5'-side of the another R2 region;
   a third oligonucleotide having 10 to 200 base pairs and comprising a region F3 having a nucleotide sequence complementary to the region F3c; and
   a fourth oligonucleotide having 10 to 200 base pairs and comprising another region R3 having the same nucleotide sequence as the region R3;
   wherein said primer set does not include a restriction enzyme and wherein each of the regions is at least 10 bases long.

4. The kit according to claim 1, wherein the second oligonucleotide is free of a promoter recognized by RNA polymerase.

5. The primer set according to claim 3, wherein the second oligonucleotide is free of a promoter recognized by RNA polymerase.

6. The kit according to claim 1, wherein the first oligonucleotide is free of a promoter recognized by RNA polymerase, and the kit does not include a restriction enzyme.

7. The primer set according to claim 3, wherein the first oligonucleotide is free of a promoter recognized by RNA polymerase, and the primer set does not include a restriction enzyme.

8. The kit according to claim 1, wherein the complementary chain synthesized with the second oligonucleotide comprises another region R1c at the 5' terminal thereof and another region R1 that is complementary to the another region R1c.

* * * * *

UNITED STATES PATENT AND TRADEMARK OFFICE
CERTIFICATE OF CORRECTION

PATENT NO.        : 9,909,168 B2
APPLICATION NO.   : 12/331196
DATED             : March 6, 2018
INVENTOR(S)       : Tsugunori Notomi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 852 days.

Signed and Sealed this
Twenty-third Day of October, 2018

Andrei Iancu
*Director of the United States Patent and Trademark Office*

SEQUENCE LISTING

```
<160> NUMBER OF SEQ ID NOS: 29

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 1
cgactctaga ggatccccgg gtactttttg ttgtgtggaa ttgtgagcgg at           52

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 2
acaacgtcgt gactgggaaa acccttttg tgcgggcctc ttcgctatta c             51

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      Artificially synthesized primer sequence
```

<400> SEQUENCE: 3 acttatgct tccggctcgt a                                              21

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 4
gttgggaagg gcgatcg                                                  17

<210> SEQ ID NO 5
<211> LENGTH: 600
<212> TYPE: DNA
<213> ORGANISM: Bacteriophage M13mp18

<400> SEQUENCE: 5
gcgcccaata cgcaaaccgc ctctccccgc gcgttggccg attcattaat gcagctggca    60
cgacaggttt cccgactgga aagcgggcag tgagcgcaac gcaattaatg tgagttagct   120
cactcattag gcaccccagg ctttacactt tatgcttccg gctcgtatgt tgtgtggaat   180
tgtgagcgga taacaatttc acacaggaaa cagctatgac catgattacg aattcgagct   240
cggtacccgg ggatcctcta gagtcgacct gcaggcatgc aagcttggca ctggccgtcg   300
ttttacaacg tcgtgactgg gaaaaccctg gcgttaccca acttaatcgc cttgcagcac   360
atcccccttt cgccagctgg cgtaatagcg aagaggcccg caccgatcgc ccttcccaac   420
agttgcgcag cctgaatggc gaatggcgct ttgcctggtt tccggcacca gaagcggtgc   480
cggaaagctg gctggagtgc gatcttcctg aggccgatac ggtcgtcgtc ccctcaaact   540
ggcagatgca cggttacgat gcgcccatct acaccaacgt aacctatccc attacggtca   600

<210> SEQ ID NO 6
<211> LENGTH: 63
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 6
ctcttccaaa agtaaggcag gaaatgtgaa accagatcgt aatttggaag acccagcatc    60
cag                                                                  63

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 7
gtggattcgc actcctcccg ctgatcggga cctgcctcgt cgt                      43

<210> SEQ ID NO 8
<211> LENGTH: 16
<212> TYPE: DNA
<213> ORGANISM: Artificial Sequence

```
<220> FEATURE:
<223> OTHER INFORMATION: Description of Artificial Sequence:
      Artificially synthesized primer sequence

<400> SEQUENCE: 8
gccacctggg tgggaa                                                        16

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 9
ggcgagggag ttcttcttct ag                                                 22

<210> SEQ ID NO 10
<211> LENGTH: 430
<212> TYPE: DNA
<213> ORGANISM: Hepatitis B virus

<400> SEQUENCE: 10
ctccttgaca ccgcctctgc tctgtatcgg gaggccttag agtctccgga acattgttca        60
cctcaccata cagcactcag gcaagctatt ctgtgttggg gtgagttaat gaatctggcc       120
acctgggtgg gaagtaattt ggaagaccca gcatccaggg aattagtagt cagctatgtc       180
aatgttaata tgggcctaaa aatcagacaa ctattgtggt ttcacatttc ctgccttact       240
tttggaagag aaactgtttt ggagtatttg gtatcttttg gagtgtggat tcgcactcct       300
cccgcttaca gaccaccaaa tgcccctatc ttatcaacac ttccggaaac tactgttgtt       360
agacgacgag gcaggtcccc tagaagaaga actccctcgc ctcgcagacg aaggtctcaa       420
tcgccgcgtc                                                              430

<210> SEQ ID NO 11
<211> LENGTH: 293
<212> TYPE: DNA
<213> ORGANISM: Artificial Sequence
<220> FEATURE:
<223> OTHER INFORMATION: Description of Artificial Sequence:
      Artificially synthesized sequence

<400> SEQUENCE: 11
acaacgtcgt gactgggaaa accctttttg tgcgggcctc ttcgctatta cgccagctgg        60
cgaaaggggg atgtgctgca aggcgattaa gttgggtaac gccagggttt tcccagtcac       120
gacgttgtaa aacgacggcc agtgccaagc ttgcatgcct gcaggtcgac tctagaggat       180
ccccgggtac cgagctcgaa ttcgtaatca tggtcatagc tgtttcctgt gtgaaattgt       240
tatccgctca caattccaca acaaaaaag tacccgggga tcctctagag tcg              293

<210> SEQ ID NO 12
<211> LENGTH: 293
<212> TYPE: DNA
<213> ORGANISM: Artificial Sequence
<220> FEATURE:
<223> OTHER INFORMATION: Description of Artificial Sequence:
      Artificially synthesized sequence
```

```
<400> SEQUENCE: 12
cgactctaga ggatccccgg gtacttttg ttgtgtggaa ttgtgagcgg ataacaattt      60
cacacaggaa acagctatga ccatgattac gaattcgagc tcggtacccg ggatcctct    120 agagtcgacc tgcaggcatg caagcttggc actggccgtc gttttacaac gtcgtgactg   180
ggaaaaccct ggcgttaccc aacttaatcg ccttgcagca catccccctt cgccagctg    240 gcgtaatagc gaagaggccc gcacaaaaag ggttttccca gtcacgacgt tgt           293

<210> SEQ ID NO 13
<211> LENGTH: 459
<212> TYPE: DNA
<213> ORGANISM: Artificial Sequence
<220> FEATURE:
<223> OTHER INFORMATION: Description of Artificial Sequence:
      Artificially synthesized sequence

<400> SEQUENCE: 13
acaacgtcgt gactgggaaa accctttttg tgcgggcctc ttcgctatta cgccagctgg    60
cgaaaggggg atgtgctgca aggcgattaa gttgggtaac gccagggttt tcccagtcac   120
gacgttgtaa aacgacggcc agtgccaagc ttgcatgcct gcaggtcgac tctagaggat   180
ccccgggtac cgagctcgaa ttcgtaatca tggtcatagc tgtttcctgt gtgaaattgt   240
tatccgctca caattccaca acaaaaaag tacccgggga tcctctagag tcgacctgca    300
ggcatgcaag cttggcactg gccgtcgttt tacaacgtcg tgactgggaa accctggcg    360 ttacccaact taatcgcctt gcagcacatc ccccttcgc cagctggcgt aatagcgaag    420
aggcccgcac aaaaagggtt tcccagtca cgacgttgt                           459

<210> SEQ ID NO 14
<211> LENGTH: 458
<212> TYPE: DNA
<213> ORGANISM: Artificial Sequence
<220> FEATURE:
<223> OTHER INFORMATION: Description of Artificial Sequence:
      Artificially synthesized sequence

<400> SEQUENCE: 14
cgactctaga ggatccccgg gtacttttg ttgtgtggaa ttgtgagcgg ataacaattt      60
cacacaggaa acagctatga ccatgattac gaattcgagc tcggtacccg ggatcctct    120 agagtcgacc tgcaggcatg caagcttggc actggccgtc gttttacaac gtcgtgactg   180
ggaaaaccct ggcgttaccc aacttaatcg ccttgcagca catccccctt cgccagctg    240 gcgtaatagc gaagaggccc gcacaaaaag ggttttccca gtcacgacgt tgtaaaacga   300
cggccagtgc caagcttgca tgcctgcagg tcgactctag aggatccccg ggtaccgagc   360
tcgaattcgt aatcatggtc atagctgttt cctgtgtgaa attgttatcc gctcacaatt   420
ccacacaaca aaaagtaccc ggggatcctc tagagtcg                           458

<210> SEQ ID NO 15
<211> LENGTH: 790
<212> TYPE: DNA
<213> ORGANISM: Artificial Sequence
<220> FEATURE:
<223> OTHER INFORMATION: Description of Artificial Sequence:
      Artificially synthesized sequence
```

<400> SEQUENCE: 15

```
acaacgtcgt gactgggaaa acccttttg tgcgggcctc ttcgctatta cgccagctgg    60
cgaaaggggg atgtgctgca aggcgattaa gttgggtaac gccagggttt tcccagtcac   120
gacgttgtaa aacgacggcc agtgccaagc ttgcatgcct gcaggtcgac tctagaggat   180
ccccgggtac cgagctcgaa ttcgtaatca tggtcatagc tgtttcctgt gtgaaattgt   240
tatccgctca caattccaca acaaaaaag tacccggga tcctctagag tcgacctgca    300
ggcatgcaag cttggcactg gccgtcgttt tacaacgtcg tgactgggaa aaccctggcg   360
ttacccaact taatcgcctt gcagcacatc ccccttcgc cagctggcgt aatagcgaag   420
aggcccgcac aaaaagggtt tcccagtca cgacgttgta aaacgacggc cagtgccaag    480
cttgcatgcc tgcaggtcga ctctagagga tccccgggta cttttttgttg tgtgaattg   540
tgagcggata caatttcac acaggaaaca gctatgacca tgattacgaa ttcgagctcg   600
gtacccgggg atcctctaga gtcgacctgc aggcatgcaa gcttggcact ggccgtcgtt   660
ttacaacgtc gtgactggga aaaccctggc gttacccaac ttaatcgcct tgcagcacat   720
cccccttcg ccagctggcg taatagcgaa gaggcccgca caaaagggt tttcccagtc    780
acgacgttgt                                                          790
```

<210> SEQ ID NO 16
<211> LENGTH: 789
<212> TYPE: DNA
<213> ORGANISM: Artificial Sequence
<220> FEATURE:
<223> OTHER INFORMATION: Description of Artificial Sequence:
      Artificially synthesized sequence

<400> SEQUENCE: 16

```
cgactctaga ggatccccgg gtactttttg ttgtgtggaa ttgtgagcgg ataacaattt    60
cacacaggaa acagctatga ccatgattac gaattcgagc tcggtacccg ggatcctct   120
agagtcgacc tgcaggcatg caagcttggc actggccgtc gttttacaac gtcgtgactg   180
ggaaaaccct ggcgttaccc aacttaatcg ccttgcagca catccccctt cgccagctg    240
gcgtaatagc gaagaggccc gcacaaaaag gttttccca gtcacgacgt tgtaaaacga   300
cggccagtgc caagcttgca tgcctgcagg tcgactctag aggatccccg ggtaccgagc   360
tcgaattcgt aatcatggtc atagctgttt cctgtgtgaa attgttatcc gctcacaatt   420
ccacacaaca aaaagtaccc ggggatcctc tagagtcgac ctgcaggcat gcaagcttgg   480
cactggccgt cgttttacaa cgtcgtgact gggaaaaccc ttttgtgcg ggcctcttcg    540
ctattacgcc agctggcgaa aggggatgt gctgcaaggc gattaagttg gtaacgcca    600
gggttttccc agtcacgacg ttgtaaaacg acggccagtg ccaagcttgc atgcctgcag   660
gtcgactcta ggatccccc gggtaccgag ctcgaattcg taatcatggt catagctgtt    720
tcctgtgtga aattgttatc cgctcacaat tccacacaac aaaaagtacc cggggatcct   780
ctagagtcg                                                           789
```

<210> SEQ ID NO 17
<211> LENGTH: 310
<212> TYPE: DNA
<213> ORGANISM: Artificial Sequence
<220> FEATURE:
<223> OTHER INFORMATION: Description of Artificial Sequence:
      Artificially synthesized sequence

<400> SEQUENCE: 17

```
gtggattcgc actcctcccg ctgatcggga cctgcctcgt cgtctaacaa cagtagtttc    60
cggaagtgtt gataagatag gggcatttgg tggtctgtaa gcgggaggag tgcgaatcca   120
cactccaaaa gataccaaat actccaaaac agtttctctt ccaaaagtaa ggcaggaaat   180
gtgaaaccac aatagttgtc tgattttag gcccatatta acattgacat agctgactac   240
taattccctg gatgctgggt cttccaaatt acgatctggt ttcacatttc ctgccttact   300
tttggaagag                                                          310
```

<210> SEQ ID NO 18
<211> LENGTH: 465
<212> TYPE: DNA
<213> ORGANISM: Artificial Sequence
<220> FEATURE:
<223> OTHER INFORMATION: Description of Artificial Sequence:
      Artificially synthesized sequence

<400> SEQUENCE: 18

```
gtggattcgc actcctcccg ctgatcggga cctgcctcgt cgtctaacaa cagtagtttc    60
cggaagtgtt gataagatag gggcatttgg tggtctgtaa gcgggaggag tgcgaatcca   120
cactccaaaa gataccaaat actccaaaac agtttctctt ccaaaagtaa ggcaggaaat   180
gtgaaaccac aatagttgtc tgattttag gcccatatta acattgacat agctgactac   240
taattccctg gatgctgggt cttccaaatt acgatctggt ttcacatttc ctgccttact   300
tttggaagag aaactgtttt ggagtatttg gtatcttttg gagtgtggat tcgcactcct   360
cccgcttaca gaccaccaaa tgcccctatc ttatcaacac ttccggaaac tactgttgtt   420
agacgacgag gcaggtcccg atcagcggga ggagtgcgaa tccac                   465
```

<210> SEQ ID NO 19
<211> LENGTH: 20
<212> TYPE: DNA
<213> ORGANISM: Bacteriophage M13mp18

<400> SEQUENCE: 19

```
ccggggatcc tctagagtcg                                               20
```

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:
      Mutant form of M13mp18

<400> SEQUENCE: 20

```
ccggggatcc tctagagtca                                               20
```

<210> SEQ ID NO 21
<211> LENGTH: 48
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 21

```
cgactctaga ggatccccgg ttttgttgt gtggaattgt gagcggat                 48
```

-continued

```
<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 22
tgactctaga ggatccccgg tttttgttgt gtggaattgt gagcggat        48

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 23
cgtcgtgact gggaaaaccc tttttgtgcg ggcctcttcg ctattac         47

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 24
actttatgct tccggctcgt a                                     21

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 25
gttgggaagg gcgatcg                                          17

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 26
tgttcctgat gcagtgggca gctttagtct gcggcggtgt tctg            44

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 27
tgctgggtcg gcacagcctg aagctgacct gaaatacctg gcctg           45
```

```
<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 28
tgcttgtggc ctctcgtg                                                    18

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence:
      Artificially synthesized primer sequence

<400> SEQUENCE: 29
gggtgtggga agctgtg                                                     17
```